United States Patent
Fox et al.

(10) Patent No.: US 11,351,350 B2
(45) Date of Patent: Jun. 7, 2022

(54) APPARATUS FOR CONNECTING A TUBE CONNECTOR TO A FITTING AND TO FASTEN OR UNFASTEN CLOSURE CAPS

(71) Applicant: PERIPAL AG, Zurich (CH)

(72) Inventors: Stephan Fox, Zurich (CH); Mirko Meboldt, Zurich (CH); Sandra Neumann, Zurich (CH)

(73) Assignee: PERIPAL AG, Zurich (CH)

( * ) Notice: Subject to any disclaimer, the term of this patent is extended or adjusted under 35 U.S.C. 154(b) by 758 days.

(21) Appl. No.: 15/580,392

(22) PCT Filed: Jun. 8, 2016

(86) PCT No.: PCT/EP2016/063086
§ 371 (c)(1),
(2) Date: Dec. 7, 2017

(87) PCT Pub. No.: WO2016/198486
PCT Pub. Date: Dec. 15, 2016

(65) Prior Publication Data
US 2018/0161567 A1    Jun. 14, 2018

(30) Foreign Application Priority Data

Jun. 8, 2015   (WO) .................. PCT/EP2015/062745
Aug. 31, 2015  (WO) .................. PCT/EP2015/069878

(51) Int. Cl.
*A61M 39/10*     (2006.01)
*A61M 39/08*     (2006.01)
(Continued)

(52) U.S. Cl.
CPC ...... *A61M 39/1011* (2013.01); *A61M 39/162* (2013.01); *A61M 39/165* (2013.01);
(Continued)

(58) Field of Classification Search
CPC ........ A61M 1/285; A61M 1/28; A61M 1/282; A61M 2039/1027; A61M 2039/1083;
(Continued)

(56) References Cited

U.S. PATENT DOCUMENTS 465,575 A   12/1891  Tyman
498,146 A   5/1893   Woolley
(Continued)

FOREIGN PATENT DOCUMENTS

CA    2574551       7/2008
CN    101918075 A   12/2010
(Continued)

*Primary Examiner* — Nathan R Price
*Assistant Examiner* — Tasnim Mehjabin Ahmed
(74) *Attorney, Agent, or Firm* — JMB Davis Ben-David

(57) ABSTRACT

An apparatus is provided for connecting and disconnecting a tubular fitting connector to a fluid conduit. A cradle assembly accommodates the fluid conduit, and includes a body having a first port and a second port. The first and second ports are disposed at opposite ends of the body, and each port is configured for receiving an end cap of the tubular fitting to fasten or unfasten the end cap for replacement. A connector holder is disposed between the first and second ports, and is configured for accommodating insertion of the connector. A holder assembly is provided for accommodating insertion of the tubular fitting. The cradle assembly is reciprocable relative to the holder assembly for transitioning the cradle assembly between a first position, a second position, and a third position.

30 Claims, 25 Drawing Sheets

(51) Int. Cl.
*A61M 39/16* (2006.01)
*A61M 39/22* (2006.01)
*A61M 25/00* (2006.01)

(52) U.S. Cl.
CPC ... *A61M 25/0021* (2013.01); *A61M 2039/087* (2013.01); *A61M 2039/1066* (2013.01); *A61M 2039/1072* (2013.01); *A61M 2039/1077* (2013.01); *A61M 2039/224* (2013.01); *A61M 2205/106* (2013.01)

(58) Field of Classification Search
CPC .. A61M 2039/1088; A61M 2039/1077; A61M 39/10; A61M 39/105; A61M 39/162; A61M 39/18
See application file for complete search history.

(56) References Cited

U.S. PATENT DOCUMENTS

| | | | |
|---|---|---|---|
| 524,830 A | 8/1894 | Leggo | |
| 550,991 A | 12/1895 | Meyer | |
| 561,150 A | 6/1896 | Whipple | |
| 595,789 A | 12/1897 | Smith | |
| 629,392 A | 12/1898 | Protheroe | |
| 4,396,382 A * | 8/1983 | Goldhaber | A61M 1/1668 604/28 |
| 4,440,207 A | 4/1984 | Genatempo | |
| 4,655,753 A * | 4/1987 | Bellotti | A61M 39/18 604/29 |
| 4,981,469 A | 1/1991 | Whitehouse | |
| 5,248,306 A | 9/1993 | Clark | |
| 5,509,911 A * | 4/1996 | Cottone, Sr. | A61M 39/1055 604/536 |
| 5,611,506 A | 3/1997 | Berger | |
| 5,620,427 A * | 4/1997 | Werschmidt | A61M 39/10 137/516.13 |
| 5,957,894 A | 9/1999 | Kerwin | |
| 6,293,921 B1 * | 9/2001 | Shinmoto | A61M 1/28 604/29 |
| 6,485,483 B1 * | 11/2002 | Fujii | A61M 1/28 604/535 |
| 2004/0011826 A1 | 1/2004 | Stradella | |
| 2005/0120523 A1 | 6/2005 | Schweikert | |
| 2007/0073215 A1 * | 3/2007 | Wieslander | A61M 39/18 604/29 |
| 2009/0012448 A1 * | 1/2009 | Childers | A61M 1/14 604/29 |
| 2009/0028750 A1 | 1/2009 | Ryan | |
| 2010/0286625 A1 * | 11/2010 | Arduini | A61M 39/10 604/246 |
| 2012/0022469 A1 | 1/2012 | Alpert | |
| 2012/0229237 A1 | 9/2012 | Zhao | |
| 2013/0338642 A1 | 12/2013 | Maulin | |
| 2014/0207118 A1 | 7/2014 | Tsoukalis | |
| 2014/0303595 A1 | 10/2014 | Justus | |
| 2015/0112249 A1 | 4/2015 | Ahn et al. | |
| 2015/0297814 A1 | 10/2015 | Zanini | |
| 2015/0335806 A1 | 11/2015 | Rada | |

FOREIGN PATENT DOCUMENTS

| | | |
|---|---|---|
| CN | 103127575 | 6/2013 |
| CN | 203507186 U | 4/2014 |
| CN | 203736599 U | 7/2014 |
| CN | 203936086 | 11/2014 |
| EP | 0070087 | 1/1983 |
| EP | 1841495 B1 | 12/2009 |
| EP | 2205308 B1 | 5/2014 |
| EP | 2857730 | 4/2015 |
| FR | 2096680 | 12/1973 |
| GB | 530587 | 12/1940 |
| GB | 2161709 | 10/1988 |
| JP | H08155025 | 9/1999 |
| JP | 2007535338 | 12/2007 |
| WO | 8910147 | 11/1989 |
| WO | 9902205 A1 | 1/1999 |
| WO | 9913938 | 3/1999 |
| WO | 2005016443 | 2/2005 |
| WO | 2005079890 | 10/2007 |
| WO | 2009044364 | 4/2009 |
| WO | 2009070566 A1 | 6/2009 |
| WO | 2010059968 A2 | 5/2010 |
| WO | 2012000554 | 1/2012 |
| WO | 2013175371 | 11/2013 |
| WO | 2014001310 | 1/2014 |
| WO | 2014121677 A1 | 8/2014 |
| WO | 2014159346 | 10/2014 |
| WO | 2015065958 | 5/2015 |
| WO | 2015081201 | 6/2015 |
| WO | 2016198129 | 12/2016 |

* cited by examiner

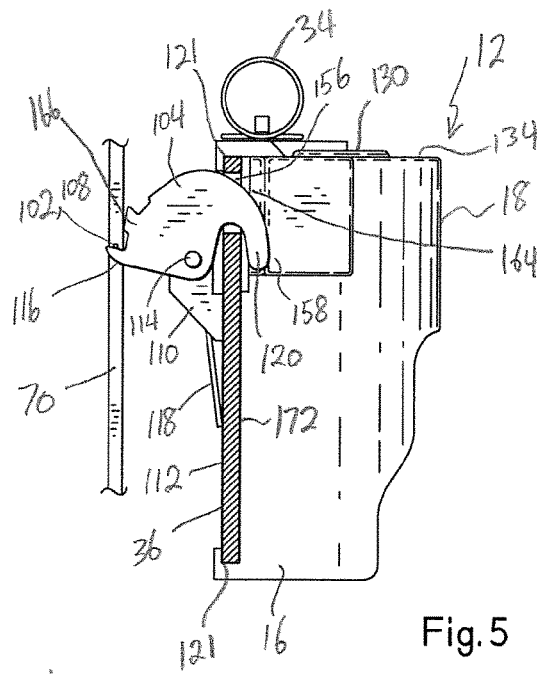
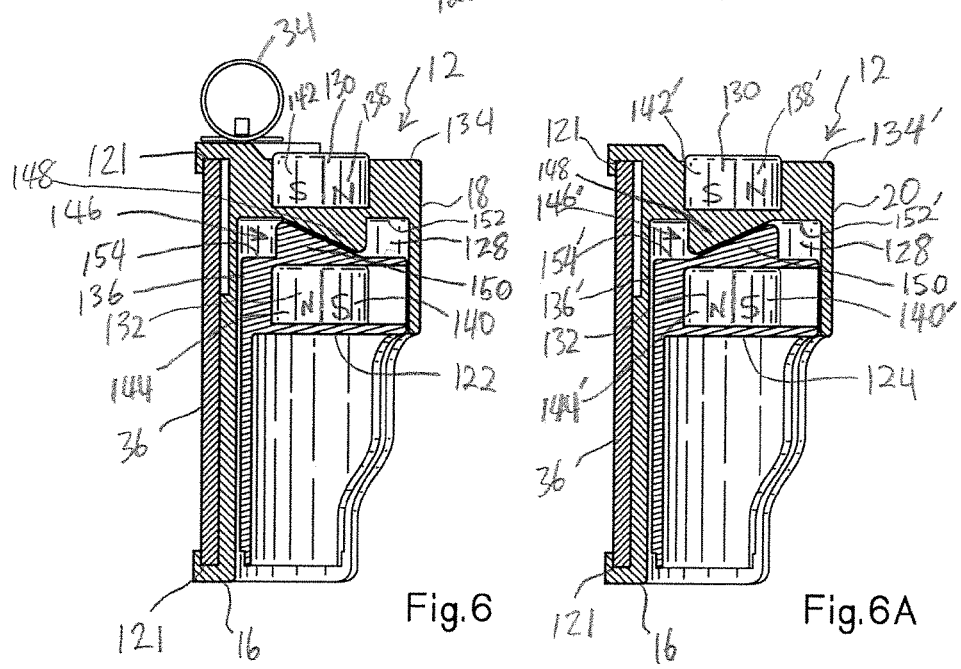
Fig. 5
Fig. 6
Fig. 6A

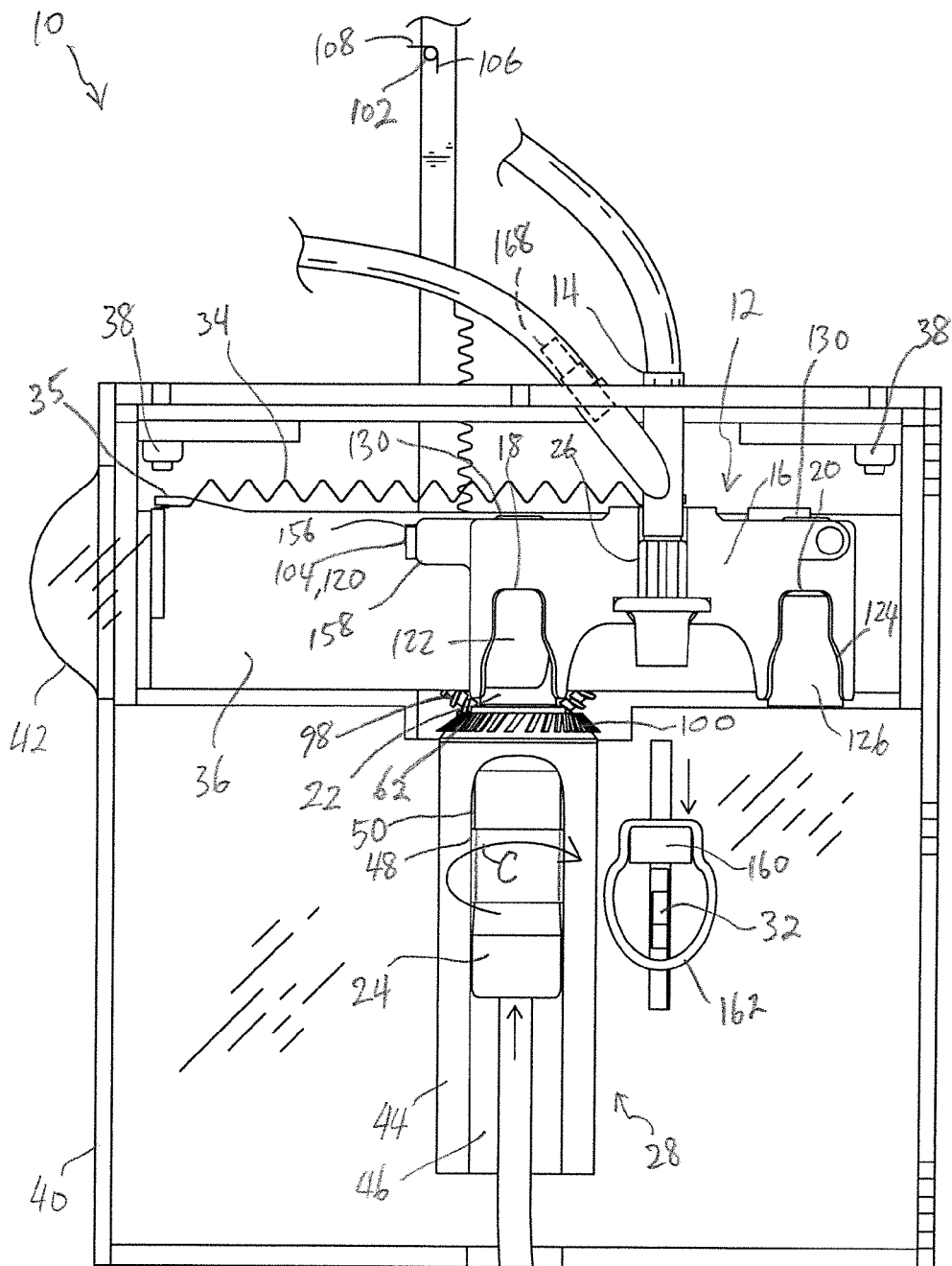
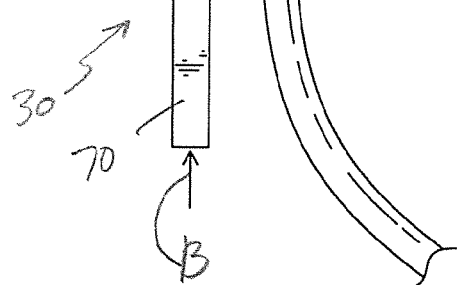

APPARATUS FOR CONNECTING A TUBE CONNECTOR TO A FITTING AND TO FASTEN OR UNFASTEN CLOSURE CAPS

CROSS-REFERENCE TO RELATED APPLICATIONS

This is the U.S. National Stage of International Application No. PCT/EP2016/063086 filed on Jun. 8, 2016, which was published under PCT Article 21(2), which in turn claims the benefit of International Patent Application Nos. PCT/EP2015/062745 filed on Jun. 8, 2015 and PCT/EP2015/069878 filed Aug. 31, 2015.

BACKGROUND

The present disclosure generally relates to connecting devices used for medical purposes, and more specifically to an apparatus for replacing a catheter cap in a protective and sterile environment.

Connections of tubular fittings for active fluidic delivery are often achieved by luer-lock connecting systems. Often, these conventional luer-lock connecting systems are used to perform peritoneal dialysis and the like by employing an actuating station having a pumping mechanism and associated flexible tubes or using manual therapy approaches. A user connects and disconnects a catheter (or similar tubing, i.e. transfer set) from the user to the connecting system at least once a day, or up to five times a day for exchanging medical fluid to and from the user's peritoneal cavity. To initiate the peritoneal dialysis, an old, existing cap of the catheter is initially disconnected from the catheter, and a connection is made between the catheter and a dialysate fluid bag, or a tubing leading to a fluid or a drug delivery system (e.g. pump). For example, a stability barrier of the fluid bag is removed, and the catheter is rotationally fastened to an end tube of the fluid bag. After completion of the dialysis, the user rotationally unfastens the catheter from the fluid bag and reseals the catheter with a new, sterile cap.

However, during exchanges of the catheter caps from an old one to a new one, the catheter and the fluid bag connection are typically exposed to an unsterile environment. At times, peritonitis can occur due to contamination caused by contact with the surrounding atmosphere, and accidental touching of the catheter. Other catheter related infections can also occur due to touch or air contact during the connection and disconnection of the connecting system. This situation is undesirable to the user because bacteria and other micro-organisms can be introduced into the user's peritoneal cavity, thereby causing peritonitis or other illness. Moreover, the conventional system relies in part on the vision and/or skills of the user for properly connecting and disconnecting the catheter.

Thus, there is a need for developing an improved connecting system that provides replacement or interchange of the catheter cap in a simpler and more reliable, sanitary manner.

SUMMARY

The present disclosure is directed to an apparatus for connecting and disconnecting a cap of a catheter using an enclosed, movable cradle assembly configured for accommodating a connector, particularly a fluid bag connector (herein the invention is often described in terms of a fluid bag connector, but may also be used with any other connector). Furthermore, particularly, the notion catheter refers to medical catheters, but particularly also to all other structures or conduits via which a fluid can be delivered and which structures or conduits can be closed with a cap. Further, particularly, the notion cap refers to all kinds of closures that can be used in a reasonable manner in the framework of the present invention.

Particularly, aspects of the present invention relate to an apparatus and method as claimed, wherein preferred embodiments are stated in the corresponding sub claims and are described below.

Particularly, the apparatus according to the present invention is designed to mechanically connect a Peritoneal Dialysis (PD) catheter to a dialysis bag during continuous ambulatory peritoneal dialysis (CAPD) procedure (and also with APD, automated peritoneal dialysis when connected to a PD cycler). The apparatus is particularly intended for use by home dialysis patients, caregivers and health care professionals at home or within health care facilities.

Further, particularly, the adapter according to the invention is designed to transform a rotational Luer movement into a linear movement so that connecting/disconnecting or fastening/unfastening can be performed in a rotation free manner by means of merely linear plugging or pulling movement.

Particularly, the adapter according to the invention is intended to mate two devices together and is—according to an embodiment—either protected by the closure cap (also denoted end cap) or connected to the dialysis bag (or any tubing connected to a drug or a drug delivery system) during the therapy. Particularly, the adapter is fastened to the catheter (or e.g. a transfer set, for instance mini-set) of the patient and particularly rests there for the e.g. 6 months said catheter (or e.g. a transfer- or mini-set) is in use.

Further, particularly, the end cap of the apparatus is intended to be used for closure of the adapter when no dialysis bag is attached to perform the therapy. Particularly, it is held in place with a secured sealed locking mechanism.

Further, particularly, the apparatus comprises a housing for receiving a body (e.g. in form of a sterile consumable) that is configured to holds the connector and end caps to be connected to the tubular fitting. Thus, this body ensures an antibacterial conduction of the connecting/disconnecting or fastening/unfastening (end caps) operations. It is preferably pre-filled/pre-assembled with the new (sterile) end cap. Prior to the connecting operation, said body may be pre-filled with a sterile end cap and is then assembled onto a moveable carrier of the cradle assembly. These components assist in connecting an e.g. PD catheter to an e.g. dialysis bag during a CAPD or APD procedure.

Particularly, the apparatus comprising the above described components is intended to be used as a patient aid in home dialysis therapy. Particularly, it supports the connection of the e.g. catheter to the e.g. dialysis bag. It performs this connection mechanically in an easy manner, therefore providing a convenient alternative to the conventional connection performed completely manually.

According to an embodiment of the apparatus according to the present invention, said holder assembly includes a body having an opening for receiving the tubular fitting.

Further, according to an embodiment of the apparatus according to the present invention, the cradle assembly is configured to be movable in each of said positions towards and away from the holder assembly by means of said means for operating the cradle and holder assembly, preferably in a direction perpendicular to said transverse direction.

Further, according to an embodiment of the apparatus according to the present invention, when the cradle assembly is in the first position, the cradle assembly is movable away from the holder assembly so as to unfasten an end cap received in the first port, which end cap is fastened to a tubular fitting, from the tubular fitting that is inserted into the holder assembly.

Further, according to an embodiment of the apparatus according to the present invention, when the cradle assembly is in the second position, the cradle assembly is movable towards the holder assembly so as to connect a connector inserted into the connector holder to a tubular fitting inserted into the holder assembly so that a flow connection is established between said connector and the tubular fitting, or wherein the cradle assembly is moveable away from the holder assembly so as to disconnect a connector inserted into the connector holder and connected to a tubular fitting that is inserted into the holder assembly from the tubular fitting.

Further, according to an embodiment of the apparatus according to the present invention, the apparatus comprises a housing.

Further, according to an embodiment of the apparatus according to the invention, said body of the cradle assembly can be (e.g. manually) released from the cradle assembly, e.g. from a movable carrier of the cradle assembly that is moveable in said positions. Preferably, the body is a consumable that can be exchanged by another body of the same configuration.

Further, in an embodiment, the holder assembly and/or the cradle assembly are removably mounted in the housing.

Further according to an embodiment of the present invention, the connected catheter-dialysis fluid line (comprising in an embodiment at least the tubular fitting and the connector as well as particularly conduits connected thereto) can be removed from the housing when the cradle assembly is in the second position and has particularly been moved towards the holder assembly, e.g. in order to allow application of the device for APD.

Preferably, the housing comprises a cover that can be opened and/or removed from the housing and is preferably at least partially or completely transparent, particularly so as to be able to observe said fastening/unfastening of the end caps and said connecting of the tubular fitting to the connector or said disconnecting of the tubular fitting from the connector.

Further, according to an embodiment of the apparatus according to the present invention, the holder assembly is configured to move together with the cradle assembly when the cradle assembly is in the second position such that a member of a tubular fitting, which tubular fitting is inserted into the holder assembly, protrudes at least partially out of the housing (e.g. through a through hole of the housing) when the tubular fitting is connected to a connector that is inserted into the cradle assembly and such that said member is arranged inside the housing (e.g. in a compartment surrounded by the housing) when said tubular fitting is disconnected from said connector, wherein said member is configured to be actuated so as to open or close the tubular fitting (or catheter) for allowing or preventing the passage of fluid through the tubular fitting.

Further, according to an embodiment of the present invention, the apparatus is configured to prevent retracting of the tubular fitting for disconnecting the latter from the connector (e.g. by preventing retracting of the holder assembly into the housing) when the tubular fitting clamp (e.g. said member of the tubular fitting described herein) is not closed.

Hence, to ensure safety, the tubular fitting/catheter cannot be opened for allowing passage of fluid through the fitting/catheter from outside the housing when the tubular fitting is not connected to the connector and is not fastened to an end cap.

Preferably, said member is a rotatable member that is actuated by rotating it (e.g. about an axis along which the tubular fitting or catheter extends), wherein upon rotation of the member the tubular fitting is either closed so that no fluid can pass through the tubular fitting or opened so that fluid can pass through the tubular fitting depending on the direction of said rotation.

Further, according to an embodiment of the apparatus according to the present invention, when the cradle assembly is in the third position, the cradle assembly is movable towards the holder assembly so as to fasten an end cap received in the second port to a tubular fitting inserted into the holder assembly so that the tubular fitting is sealed.

Further, according to an embodiment of the apparatus according to the present invention, the holder assembly is configured to move together with the cradle assembly when the cradle assembly is in the third position such that a member of a tubular fitting, which tubular fitting is inserted into the holder assembly, protrudes—at least partially—out of the housing (e.g. through said through hole of the housing) when the tubular fitting is fastened to an end cap that is received in the second port (20), wherein said member (240) can be actuated so as to close the tubular fitting (or catheter) for preventing passage of fluid through the tubular fitting.

Further, according to an embodiment of the apparatus according to the present invention, the body of the cradle assembly comprises a support for supporting a first conduit of the connector, which first conduit comprises a frangible inline seal, and for supporting a second conduit of the connector, wherein the two conduits branch off from an end section of the connector, via which end section the connector is configured to be connected to a tubular fitting.

Further, according to an embodiment of the apparatus according to the present invention, the apparatus comprises a first actuating member that is configured to be manually actuated to break said frangible inline seal when the cradle assembly is in the second position and a connector inserted into the connector holder is connected to a tubular fitting inserted into the holder assembly. Preferably, the first actuating member comprises a pushable button arranged on the housing, wherein upon pushing said button, the first actuating member moves downwards and breaks said frangible inline seal of the first conduit being supported on said support.

Further, according to an embodiment of the apparatus according to the present invention, the apparatus comprises a second actuating member that is configured to be manually actuated to interrupt the passage of fluid through a first conduit of a connector being supported on said support when the cradle assembly is in the second position and a connector inserted into the connector holder is connected to a tubular fitting inserted into the holder assembly. Preferably, the second actuating member comprises a pushable button arranged on the housing, wherein upon pushing said button, the second actuating member moves downwards and pushes the first conduit into a first slot of the support so that the first conduit is interrupted.

Further, according to an embodiment of the apparatus according to the present invention, the apparatus comprises a third actuating member that is configured to be manually actuated to interrupt the passage of fluid through a second conduit of a connector being supported on said support when the cradle assembly is in the second position and a connector inserted into the connector holder is connected to a tubular fitting inserted into the holder assembly.

Further, the third actuating member preferably comprises a pushable button arranged on the housing, wherein upon pushing said button, the third actuating member moves downwards and pushes the second conduit into a second slot of the support so that the second conduit is interrupted. Preferably, the first conduit is connected to a fluid bag and the second conduit to a fluid waste bag.

Further, according to an embodiment of the present invention, the buttons and/or actuating members are configured to remain in a different (e.g. lower position) after they have been pushed by a user, e.g. in order to indicate to the patient/user that they have already been operated.

According to an embodiment all the three buttons stay in a half-down or down position when pushed during the therapy in order to indicate to the patient that they have already been operated.

Further, according to an embodiment of the apparatus according to the present invention, said apparatus may also include all or at least one of: the tubular fitting, the end caps, and the connector. These components can be configured in the same way as described above or herein when they are comprised by the apparatus (e.g. as consumables, wherein the apparatus may be preassembled/preconfigured with such components). Further, the apparatus according to the invention may also be used in combination with other tubing lines than dialysis bags.

Further, according to an embodiment of the apparatus according to the present invention, the tubular fitting comprises a first portion. Particularly, the first portion is configured to be connected to a catheter, e.g. of a transfer-set (e.g. a mini-set). Furthermore, the tubular fitting comprises and an adjacent second portion comprising an opening for connecting with an connector or for fastening an end cap to the second portion/tubular fitting.

Further, according to an embodiment of the apparatus according to the present invention, the second portion is configured such that an end cap can be fastened to the second portion by plugging the end cap into said opening of said second portion (e.g. upon said movement of the cradle assembly towards the holder assembly when the cradle assembly is in the third position), and wherein the second portion is configured such that an end cap can be unfastened from the second portion by pulling the end cap out of said opening, (e.g. upon said movement of the cradle assembly away from the holder assembly when the cradle assembly is in the first position).

Further, according to an embodiment of the apparatus according to the present invention, said plugging and/or pulling is irrotational (i.e. does not involve any rotation of the second portion/tubular fitting or of the respective end cap).

Further, according to an embodiment of the apparatus according to the present invention, the second portion is configured such that a connector can be connected to the second portion by plugging the connector into said opening of said second portion (e.g. upon said movement of the cradle assembly towards the holder assembly when the cradle assembly is in the second position), and wherein the second portion is configured such that a connector can be disconnected from the second portion by pulling the connector out of said opening (e.g. upon said movement of the cradle assembly away from the holder assembly when the cradle assembly is in the second position).

Further, according to an embodiment of the apparatus according to the present invention, the second portion is formed as an adapter, which comprises a first recess at a first end of the adapter, which first recess comprises an internal thread configured to be rotationally fastened to an external thread of the first portion, particularly such that a lumen surrounded by the first portion is in flow communication with a lumen surrounded by the adapter. Preferably, the first recess comprises a conical shape. Further, preferably, the external thread is formed on a conical section of the first portion. Furthermore, preferably, the adapter comprises a shroud, preferably a bell-shaped shroud, at an opposite second end of the adapter, which shroud surrounds a second recess of the adapter into which second recess a protrusion of the adapter protrudes, which protrusion preferably comprises said opening of the adapter such that the shroud surrounds said protrusion and said opening of the adapter. Further, the shroud is preferably coaxially arranged with respect to said protrusion.

Further, according to an embodiment of the apparatus according to the present invention, the second portion is integrally connected to first portion, particularly such that the two portions (i.e. their lumina) are in flow communication with each other.

Further, according to an embodiment of the apparatus according to the present invention, the apparatus comprises a guiding means for guiding said movement of the cradle assembly towards and away from the holder assembly as described above. Further, according to an embodiment of the apparatus according to the present invention, said guiding means may also be configured for guiding said movement of the holder assembly.

Further, according to an embodiment of the apparatus according to the present invention, the apparatus comprises an actuating means for actuating said means for operating the cradle assembly and the holder assembly. Preferably, said actuating means comprises a handle for manually actuating said means from outside the housing.

Further, according to alternative embodiments of the apparatus described in the following, each of said ports may be configured for receiving the respective end cap of the tubular fitting to rotationally fasten or unfasten the end cap for replacement.

In an embodiment, the cradle assembly transitions between a cap-off position, a fluid-delivery position, and a cap-on position in a semi-sterile, protective enclosure during operation. An important aspect of the present apparatus is that mechanical operations of the movable cradle assembly allow replacement of an old catheter cap with a new catheter cap in the sterile, protective enclosure without the user touching the caps and/or exposing ends of a catheter and/or a fluid bag connector, thereby preventing droplet or touch infection. In an embodiment, the cradle assembly includes a horizontal, elongate body having two luer-lock ports (or cap holders) disposed at opposite ends of the body and configured for receiving an end of the catheter, and a connector holder disposed between the luer-lock ports and configured for accommodating the fluid bag connector. During operation, the cradle assembly transitions between three different positions for removing the old catheter cap, connecting to the fluid bag connector, and putting on the new catheter cap after the dialysis under a telescoping action of a pusher bar or an alternative actuating element.

As described in greater detail below, because the old catheter cap is replaced with the new catheter cap by merely pulling or pushing the pusher bar externally of the enclosure (or by actuating an alternative actuating element or means), the present apparatus simplifies the connection and disconnection of the catheter to the fluid bag and the replacement of the catheter caps. Since these operations are performed in the protective enclosure without contact, the droplet or touch infection can be substantially reduced. As such, a secure and reduced contamination application of the e.g. luer-lock connection is realized for the user.

Further, because the present apparatus is preferably made of non-rusting plastic and/or metal materials, a simpler cleaning is afforded by using a conventional washer and the like. Also, in a preferred embodiment, a transparent cover is provided for the protective enclosure so that the mechanical movement during operation is conveniently observed, and potential malfunctions of various components of the present apparatus is detected.

In one embodiment, an apparatus for connecting and disconnecting a tubular fitting to a connector includes a cradle assembly configured for accommodating the connector, the cradle assembly including an e.g. elongate body having a first port and a second port, the first and second ports being disposed at opposite ends of the body, each port configured for receiving an end cap of the tubular fitting to (e.g. rotationally or e.g. translationally) fasten or unfasten the end cap for replacement, and
a connector holder being disposed between the first and second ports, and configured for accommodating insertion of the connector. A holder assembly is configured for accommodating insertion of the tubular fitting; and a means (particularly an interface gear assembly) is configured for operating the cradle assembly and the holder assembly so that the cradle assembly is reciprocable (or can be moved back and forth) in a transverse direction relative to the holder assembly between a first position, a second position, and a third position.

In another embodiment, an apparatus is provided for connecting and disconnecting a tubular fitting to a connector, and includes a cradle assembly configured for accommodating the connector, the cradle assembly including an elongate body having a first port and a second port, the first and second ports being disposed at opposite ends of the body, at least one of the first and second ports having an insertable sleeve configured for receiving an end cap of the tubular fitting to rotationally fasten or unfasten the end cap for replacement, and a connector holder being disposed between the first and second ports, and configured for accommodating insertion of the connector. A holder assembly is configured for accommodating insertion of the tubular fitting; and an interface gear assembly is configured for operating the cradle assembly and the holder assembly. The cradle assembly is reciprocable relative to a horizontal plate for transitioning the cradle assembly between a first position, a second position, and a third position.

In still another embodiment, an apparatus for connecting and disconnecting a tubular fitting to a connector is provided, including a cradle assembly configured for accommodating the connector, the cradle assembly including a horizontal, elongate body having a first port and a second port, the first and second ports being disposed at opposite ends of the body, each port configured for receiving an end cap of the tubular fitting to rotationally fasten or unfasten the end cap for replacement, and a connector holder being disposed between the first and second ports, and configured for accommodating insertion of the connector. A holder assembly is configured for accommodating insertion of the tubular fitting, the holder assembly has a slider being slidably movable within the holder assembly for actuating the slider. An interface gear assembly is configured for operating the slider, the cradle assembly, and the holder assembly so that the cradle assembly is slidingly reciprocable relative to the holder assembly for transitioning the cradle assembly between a first position, a second position, and a third position.

Furthermore, according to a preferred embodiment, said holder assembly includes a body having an opening for receiving the tubular fitting, and a slider holder being slidably movable with a slider in said opening of said body, such that the tubular fitting is carried by said slider within said body.

Further, according to a preferred embodiment, said slider holder has an outer protrusion configured for being insertable into a slot of said body such that said outer protrusion matingly engages a slider mover of said interface gear assembly.

Further, according to a preferred embodiment, said slider has at least one inner protrusion for holding at least one indent portion of the tubular fitting.

Further, according to a preferred embodiment, said slider has at least one stop magnet, and said body has at least one corresponding stop magnet for magnetically holding said slider and said body together under the attracting force of said stop magnets.

Further, according to a preferred embodiment, said holder assembly has a rotator having at least one rotator magnet, and said slider has at least one corresponding slider magnet disposed near an upper end of said slider for magnetically coupling said rotator and said slider.

Further, according to a preferred embodiment, said interface gear assembly includes an actuating element configured to be operated for actuating said holder assembly.

Further, according to a preferred embodiment, said actuating element is configured to reciprocate relative to a gear box disposed in a housing for actuating said holder assembly, wherein particularly said actuating element is on of: a pusher bar, a lever, or a handle.

Further, according to a preferred embodiment, said actuating element has a first torsion spring for actuating a stopper connected to a horizontal plate, such that said cradle assembly sequentially transitions between the first, second, and third positions.

Further, according to a preferred embodiment, said stopper has a first finger, a second finger, and a third finger, said fingers extending from said stopper for transitioning said cradle assembly between the first, second, and third positions.

Further, according to a preferred embodiment, at least one of said first and second ports has an insertable sleeve configured for receiving the end cap of the tubular fitting.

Further, according to a preferred embodiment, at least one of said first and second ports has a one-way directional mechanism for selectively rotating said corresponding sleeve in one direction while preventing motion in an opposite direction during operation.

Further, according to a preferred embodiment, at least one of said first and second ports has at least one one-directional tooth on said corresponding port, and at least one complementary one-directional tooth on said corresponding sleeve.

Further, according to a preferred embodiment, said first port has a first sleeve being slidably insertable in said first port, and configured for receiving the end cap of the tubular fitting to rotationally unfasten the end cap from the tubular fitting.

Further, according to a preferred embodiment, said second port has a second sleeve being slidably insertable in said second port, and configured for receiving a replacement cap of the tubular fitting to rotationally fasten the replacement cap upon the tubular fitting.

Further, according to a preferred embodiment, each of said first and second ports has a set of first and second port magnets, each port magnet being divided by opposing magnetic polarities.

Further, according to a preferred embodiment, each of said first and second ports has an insertable sleeve, said first port magnet being disposed on said corresponding port, and said second port magnet being disposed on said corresponding insertable sleeve.

Further, according to a preferred embodiment, said interface gear assembly is mechanically connected to a sliding hook configured for removing a cover of the connector.

Further, according to a preferred embodiment, said cradle assembly is connected to a tension element for transitioning said cradle assembly between said first, second, and third positions.

Further, according to a preferred embodiment the cradle assembly is releasably connected to a housing of the apparatus such that it can be removed from said housing, particularly when the cradle assembly is in the second position and/or when the fitting is connected to the connector (fluid-delivery).

Further, according to a preferred embodiment, the holder assembly comprises a cylindrical body with an opening for receiving the catheter, wherein said cylindrical body, and particularly also further components connected to the cylindrical body, is/are releasably connected to the housing such that it can be removed from the housing, particularly when the cradle assembly is in the second position and/or when the fitting is connected to the connector (fluid-delivery).

Further, according to a preferred embodiment, said holder assembly includes a cylindrical body comprising an opening for receiving the tubular fitting, and a slider arranged in said opening of said body, wherein said slider is designed to hold said tubular fitting such that the latter can be carried by said slider within said body, wherein said cylindrical body comprises a guiding means for guiding a movement of the slider and of the tubular fitting when the tubular fitting is carried by the slider such that the slider and the tubular fitting translate in said opening while rotating at the same time for rotationally fasten or unfasten said end cap of the tubular fitting.

Further, according to a preferred embodiment, said guiding means comprises two helical slots formed in said cylindrical body, wherein for guiding said movement said slider engages said helical slots.

Further, according to an embodiment, said means for operating the cradle assembly and particularly holder assembly can comprise a drive or motor that is configured to automatically move the cradle assembly between said positions, and wherein particularly said drive or motor is configured to automatically move the cradle assembly in each of said positions towards and away from the holder assembly in a direction perpendicular to said transverse direction.

Further, according to an embodiment, the apparatus can comprise an electronic control unit for controlling said drive or motor, wherein said electronic control unit is preferably programmable in an embodiment so that said automatic movement of the cradle assembly (and particularly holder assembly) is programmable.

Further, according to an embodiment, the apparatus may comprise an antibacterial radiation source (e.g. an ultraviolet light source) for reducing contamination with germs.

Further, according to an embodiment, the apparatus comprises a surface comprising a disinfectant admixture, particularly comprised by a coating of said surface or an additive to a molding material of said surface in order to reduce contamination with germs.

Further, according to yet another aspect of the present invention, an apparatus for connecting and disconnecting a tubular fitting to a connector is disclosed, the apparatus comprising:

a cradle assembly configured for accommodating the connector, the cradle assembly including an elongate body having:

a first port and a second port, said first and second ports being preferably disposed at opposite ends of said body, each said port configured for receiving an end cap of the tubular fitting to rotationally fasten or unfasten the end cap for replacement, and a connector holder being preferably disposed between said first and second ports, and configured for accommodating insertion of the connector;

a holder assembly configured for accommodating insertion of the tubular fitting; and a means configured for operating said cradle assembly and said holder assembly so that said cradle assembly is reciprocable preferably in a transverse direction relative to said holder assembly between a first position, a second position, and a third position; and wherein said holder assembly includes a cylindrical body comprising an opening for receiving the tubular fitting, and a slider arranged in said opening of said body, wherein said slider is designed to hold said tubular fitting such that the latter can be carried by said slider within said body, wherein said cylindrical body comprises a guiding means for guiding a movement of the slider and of the tubular fitting, when the tubular fitting is carried by the slider, such that the slider and the tubular fitting translate in said opening while rotating at the same time for rotationally fasten or unfasten said end cap of the tubular fitting, wherein particularly said guiding means comprises two helical slots formed in said cylindrical body, wherein particularly for guiding said movement said slider engages said helical slots.

A further aspect of the present invention relates to an adapter for connecting and end region of a conduit, particularly a catheter, comprising an external thread to a connector that is configured to be plugged into an opening comprised by the adapter, so that a flow communication is established between said conduit and the connector via said adapter, wherein the adapter further comprises: a first recess at a first end of the adapter, which first recess comprises an internal thread configured to be rotationally fastened to said external thread of said conduit such that a lumen surrounded by the conduit is in flow communication with a lumen surrounded by the adapter, wherein the first recess preferably comprises a conical shape, and wherein the external thread is preferably formed on a conical end section of the conduit, and a preferably bell-shaped shroud at an opposite second end of the adapter, which shroud surrounds a second recess of the adapter into which a protrusion of the adapter protrudes, which protrusion comprises said opening of the adapter such that the shroud surrounds said protrusion and said opening of the adapter, wherein the shroud is coaxially arranged with respect to said protrusion.

Yet another aspect relates to a method for connecting and disconnecting a tubular fitting to a connector, wherein the connector is connected to a tubular fitting and/or disconnected from the tubular fitting using an apparatus according to the invention as described herein.

According to an embodiment of this method, the connecting and/or disconnecting is performed by one of: a patient using the apparatus at home (e.g. a home dialysis patient), by a caregiver using the apparatus at the patient's home or within a health care facility, by a healthcare professional using the apparatus at the patient's home or in a health care facility.

Further, according to an embodiment of the method according to the present invention, the connector comprises a first conduit, which first conduit comprises a frangible inline seal, and a second conduit, wherein the two conduits branch off from an end section of the connector, which end section is configured to be connected to the tubular fitting or disconnected from the tubular fitting, and wherein the tubular fitting comprises a member which is configured to be actuated so as to open or close the tubular fitting (or catheter) for allowing or preventing the passage of fluid through the tubular fitting, wherein the method further comprises the steps of:

providing the tubular fitting with an end cap fastened to the tubular fitting, wherein the end cap is received in the first port of the body of the cradle assembly residing in the first position, and wherein the tubular fitting is inserted into the holder assembly, moving the cradle assembly away from the holder assembly so as to unfasten the end cap from tubular fitting, moving the cradle assembly into the second position and then towards the holder assembly so as to connect the connector inserted into the connector holder to the tubular fitting and so as to push said member at least partially out of the housing, preferably opening a clamp (e.g. said member of the tubular fitting) on the tubular fitting (e.g. by allowing the patient or user to open the clamp/member on the tubular fitting) so as to drain a liquid or fluid, and closing the clamp/member thereafter, breaking the frangible inline seal using the first actuating member, flushing both conduits by letting fluid flow through the first and the second conduit while the tubular fitting is closed for preventing the passage of fluid through the tubular fitting, preferably opening the clamp (e.g. said member), e.g. by allowing the patient or user to open the clamp (e.g. said member) on the tubular fitting to let liquid or fluid flow (e.g. towards the target) before closing said clamp (e.g. member) again, interrupting the second conduit by actuating the third actuating member and opening the tubular fitting by actuating said member of the tubular fitting, preferably letting fluid pass through the first conduit, the end section, and the tubular fitting towards a target, closing the tubular fitting by actuating said member of the tubular fitting, interrupting the first conduit for preventing the passage of fluid through the first conduit by actuating the second actuating member, closing the tubular fitting for preventing the passage of fluid through the tubular fitting, preferably preventing any disconnection of the liquid of fluid line or between the tubular fitting and the connector before the tubular fitting is not closed (e.g. by an preferably mechanical detecting means that is configured to detect the opening/closing status) and preventing retraction (e.g. of the tubular fitting) into the housing in case the clamp (e.g. said member) is open. (Said detecting means may also be a mechanical means that is configured to prevent said retraction when the tubular fitting is open or said clamp or said member is open and allows the passage of fluid through the tubular fitting).

moving the cradle member away from the holder assembly so as to disconnect the connector from the tubular fitting and so as to move said member of the tubular fitting back into the housing, and moving the cradle assembly into the third position and towards the holder assembly to as to fasten an end cap received in the second port to the tubular fitting.

The foregoing and other aspects and features of the disclosure will become apparent to those of reasonable skill in the art from the following detailed description, as considered in conjunction with the accompanying drawings

BRIEF DESCRIPTION OF THE DRAWINGS

FIG. 5 is a cross-section of the movable cradle assembly in the cap-off position taken along the line 5-5 of FIG. 1 and in the direction generally indicated;

FIG. 6 is a cross-section of the movable cradle assembly taken along the line 6-6 of FIG. 1 and in the direction generally indicated;

FIG. 6A is a cross-section of the movable cradle assembly taken along the line 6A-6A of FIG. 1 and in the direction generally indicated;

FIG. 10 is a plan view of the present apparatus of FIG. 9 after insertion of the catheter into the first port of the cradle assembly;

FIGS. 20 to 26 shows the functioning of the apparatus of FIGS. 19 to 21;

DETAILED DESCRIPTION

Figure 1:
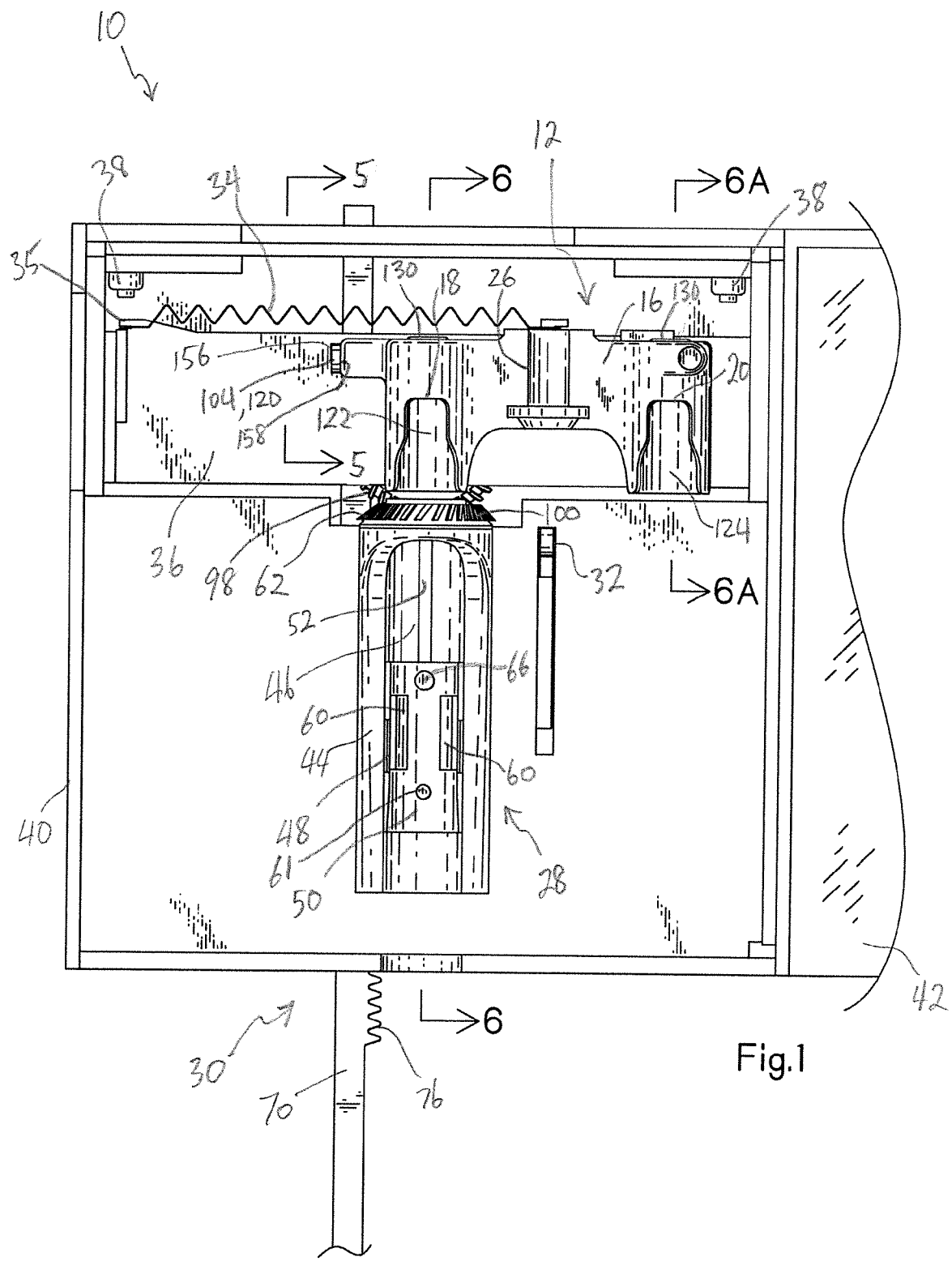
FIG. 1 is a plan view of the present apparatus, featuring a movable cradle assembly in a cap-off position, a catheter holder assembly, and a housing having an interface gear assembly underneath the cradle and catheter holder assemblies.
Figure 9:
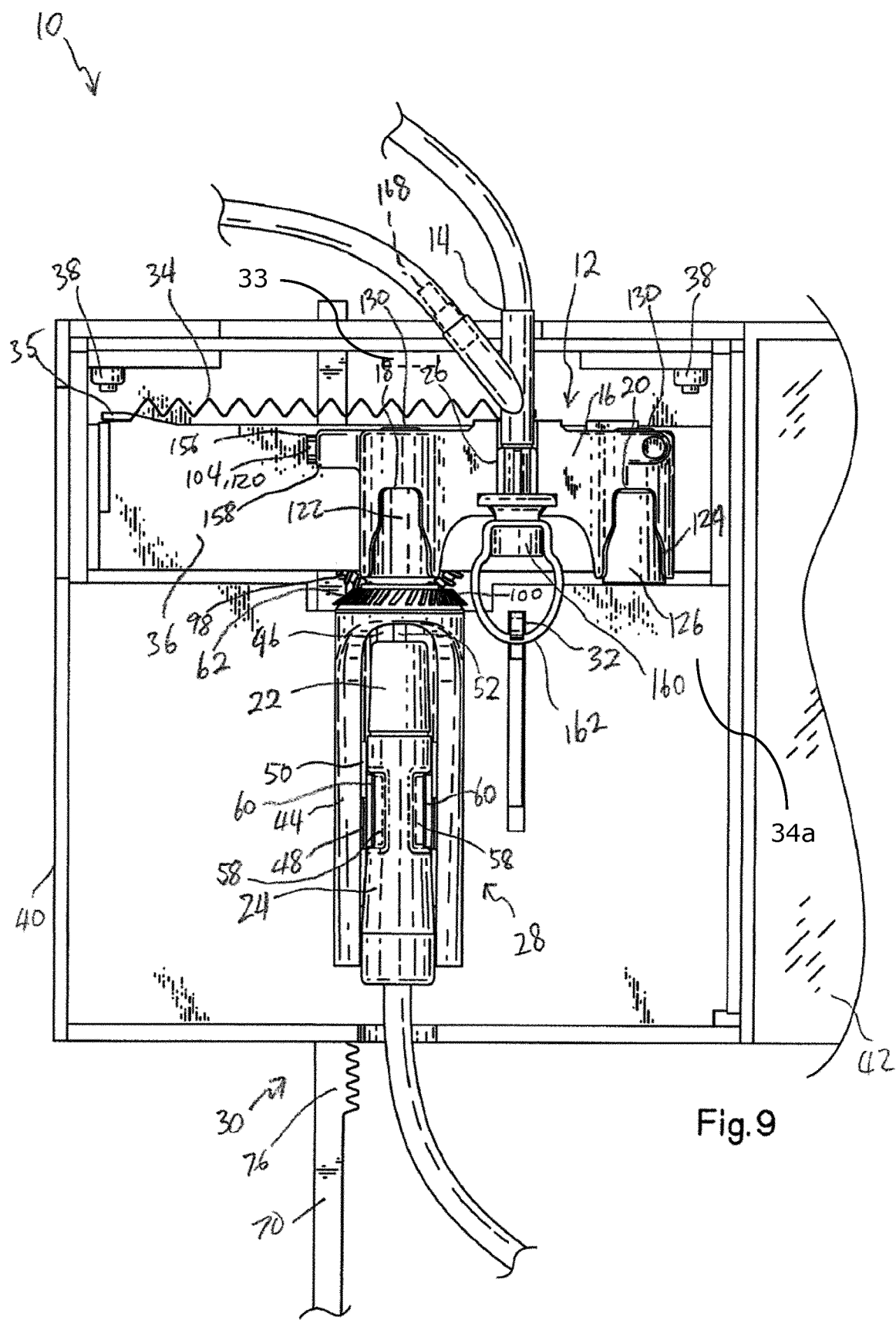
FIG. 9 is a plan view of the present apparatus of FIG. 8 after insertion of a catheter into the catheter holder assembly.

Referring now to FIGS. 1 and 9, the present apparatus is generally designated 10 and is designed to connect and disconnect tubular fittings such as medical conduits, including but not limited to catheters, often having Luer fittings or the like for performing medical procedures, such as dialysis therapies, without touching or exposing the tubular fittings in the surrounding environment. Included in the present apparatus 10 is a movable cradle assembly, generally designated 12, configured for accommodating a fluid bag connector 14 (FIG. 9). In the preferred embodiment, the fluid bag connector 14 is a dialysis bag Luer fitting or the like, but other (e.g. medical tubular) connectors are contemplated. More specifically, the cradle assembly 12 includes a horizontal, elongate body 16 having a first or left port (or cap holder) 18 and a second or right port 20, both of which are disposed at opposite ends of the body 16. Each port 18, 20 is configured for receiving an end cap 22 of a tubular fitting 24 (FIG. 9), in the preferred embodiment shown as a catheter, to rotationally fasten or unfasten the end cap of the catheter. A connector holder 26 is disposed between the first and second ports 18, 20, and configured for accommodating insertion of the fluid bag connector 14.

Also included in the present apparatus 10 are a catheter holder assembly, generally designated 28, configured for accommodating insertion of the catheter 24, and an interface gear assembly, generally designated 30, configured for operating the cradle assembly 12, the catheter holder assembly 28, and a sliding hook 32. During operation, the cradle assembly 12 is actuated under the action of a tension element or return spring 34, such as a compression spring or a resilient coil. It is preferred that the return spring 34 is attached at one end to an upper center portion of the cradle assembly 12, and at an opposite end to a leftmost corner 35 of a horizontal, elongated plate 36, such that the cradle assembly is reciprocable along the horizontal plate for transitioning the cradle assembly between three different positions, namely a cap-off position, a fluid-delivery position, and a cap-on position.

Alternatively or simultaneously, the actuation of the cradle assembly 12 is optionally performed or assisted by magnetic fields of one or more magnets 38, preferably disposed near the opposite upper corners of the apparatus 10 and the corresponding opposite ends of the body 16 of the cradle assembly. An exemplary use of the magnets 38 is described below in paragraphs relating to FIGS. 6, 6A, and 7. It is contemplated that sizes, shapes, strengths of the magnets 38 are variable to suit the application.

FIG. 1 shows that the movable cradle assembly 12 is initially positioned in the cap-off position. The cap-off position refers to a first position in which the first port 18 of the movable cradle assembly 12 is substantially longitudinally aligned with the catheter holder assembly 28 so that the first port is ready to receive and unfasten the end cap 22 of the catheter 24 (FIG. 9). Detailed transitional operations of the three positions of the present apparatus 10 are described below in paragraphs relating to FIGS. 8-16. Also, a housing 40 with a transparent cover 42 is provided for holding and supporting components of the present apparatus 10, such as the cradle, catheter holder, and interface gear assemblies 12, 28, 30. The transparent cover 42 is removable and enhances the protection of the apparatus 10 from unwanted environmental exposure, to reduce contamination.

Figure 2:
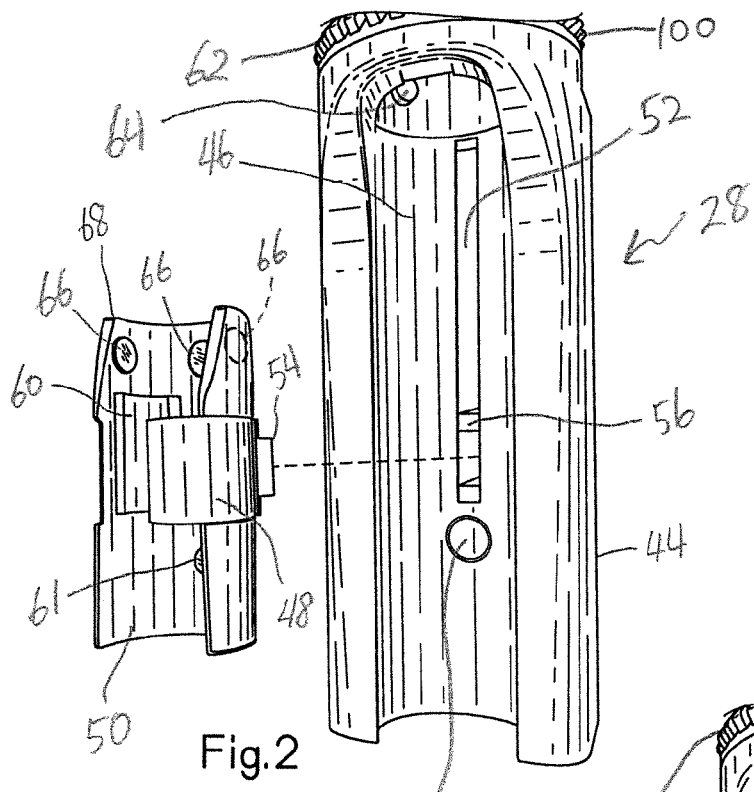
FIG. 2 is an exploded view of the catheter holder assembly of FIG. 1, featuring a slider and a slider holder.
Figure 3:
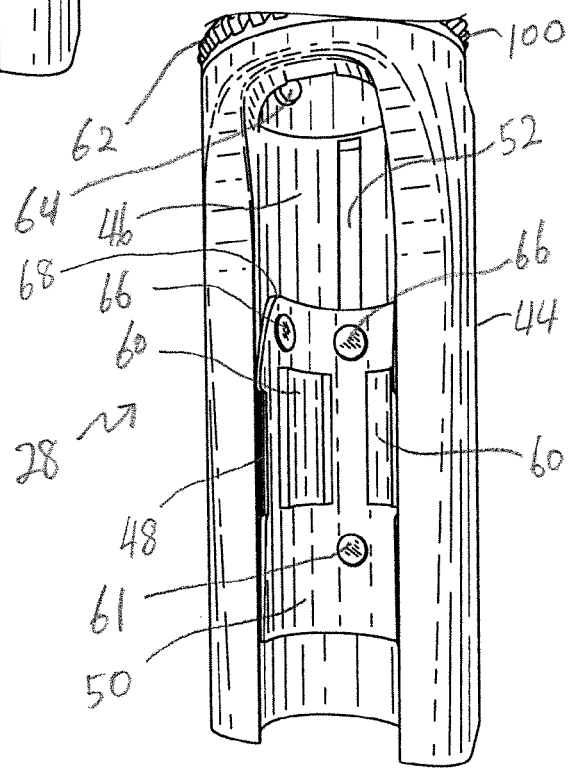
FIG. 3 is a top perspective view of the catheter holder assembly of FIG. 2 after assembly.

Referring now to FIGS. 2, 3, and 9, in a preferred embodiment, the catheter holder assembly 28 has a generally cylindrical body 44 with an opening 46 for receiving the catheter 24 (FIG. 9). It is preferred that the catheter holder assembly 28 includes a slider holder 48 being slidably movable with a slider 50 in the opening 46 of the body 44 of the catheter holder assembly 28, such that the catheter 24 is actuated by the slider along a vertical slot 52 of the body 44, and reciprocates along a longitudinal axis of the catheter holder assembly.

Preferably, the slider holder 48 has an outer protrusion 54 (FIG. 2) configured for being insertable into the slot 52 of the body 44, and the outer protrusion matingly engages a slider mover 56 (FIGS. 2 and 4) of the interface gear assembly 30. As a result, the slider holder 48 is mechanically coupled to the slider mover 56, and the catheter 24 held in the slider 50 vertically reciprocates along the longitudinal axis of the catheter holder assembly 28. Locking or securing of the catheter 24 in the slider 50 is achieved by substantially wrapping around or holding opposite indent portions 58 (FIG. 9) of the catheter with at least one inner protrusion 60 of the slider 50. Optionally, the slider 50 has at least one stop magnet 61 (FIG. 2), and the body 44 of the catheter holder assembly 28 has at least one complementary stop magnet 61 for magnetically holding the slider and the body together under the attracting force of the two stop magnets 61.

Also included in the catheter holder assembly 28 is a rotator 62 having at least one rotator magnet 64 configured for being magnetically coupled to at least one corresponding slider magnet 66 disposed near an upper end 68 of the slider 50 in a magnetically complementary relation to each other for rotating the slider during replacement of the end cap 22 of the catheter 24. Detailed operations of the rotator 62 are described below in paragraphs relating to FIGS. 8-16.

Figure 4:
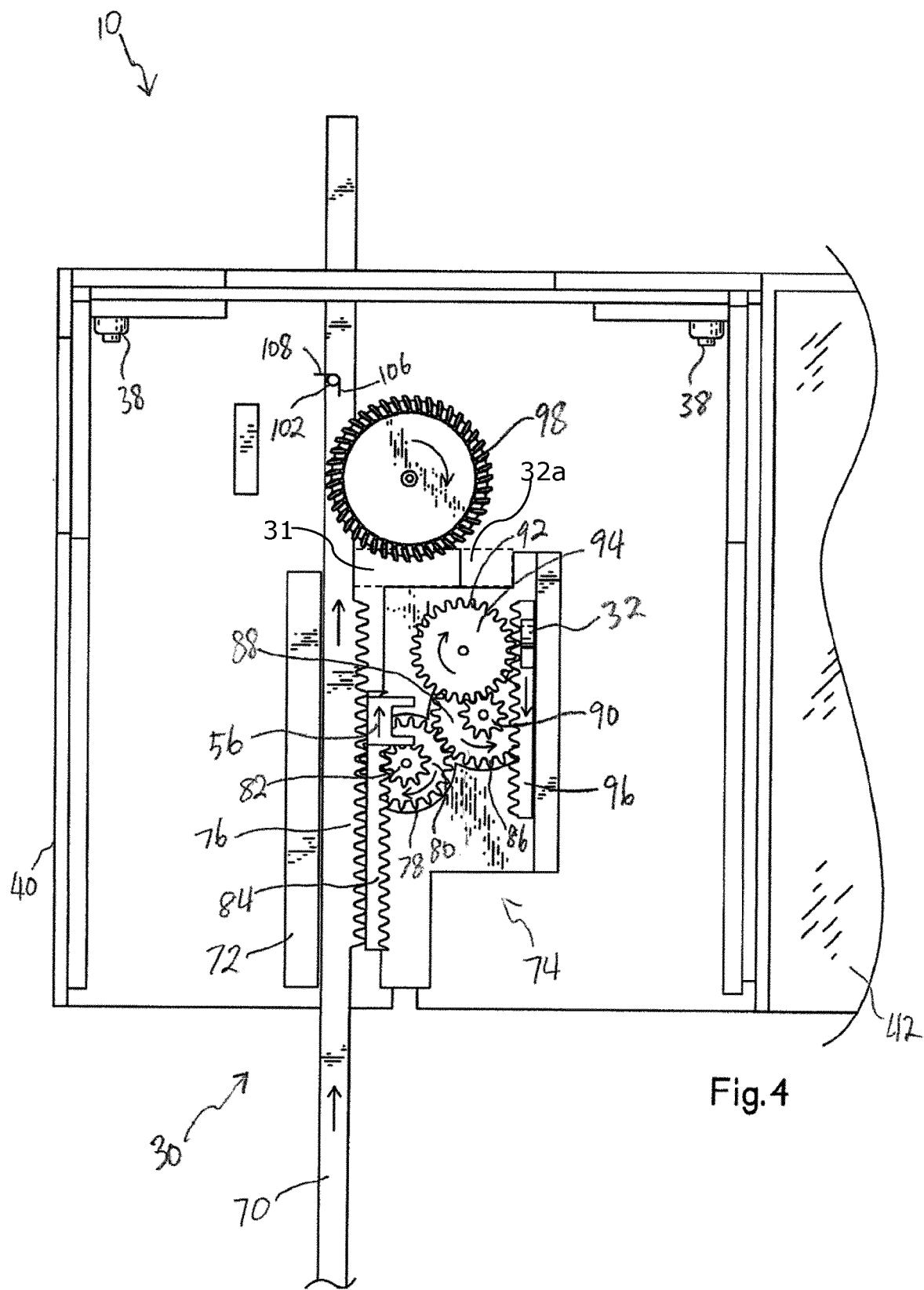
FIG. 4 is a plan view of the interface gear assembly of FIG. 1 without showing the cradle and catheter holder assemblies.

Referring now to FIGS. 1 and 4, in a preferred embodiment, the interface gear assembly 30 includes a pusher bar 70 (or an alternative actuating element) configured to reciprocate within a gear box 72 attached to the housing 40 for actuating the catheter holder assembly 28 and the sliding hook 32 using a toothed transmission, generally designated 74. As an example only, it is preferred that the pusher bar 70 includes a first rack gear 76 having a set of teeth for engaging a first set of teeth 78 of a first pinion gear wheel 80. A second set of teeth 82 axially spaced from the first set of teeth 78 of the first pinion gear wheel 80 engages a second rack gear 84 connected to the slider mover 56 for actuating the slider 50.

During operation, as the first pinion gear wheel 80 is rotated by the pusher bar 70, the first set of teeth 78 of the first pinion gear wheel engages a first set of teeth 86 of a second pinion gear wheel 88. A second set of teeth 90 axially spaced from the first set of teeth 86 of the second pinion gear wheel 88 engages a first set of teeth 92 of a third pinion gear wheel 94. In turn, the first set of teeth 92 of the third pinion gear wheel 94 engages a third rack gear 96 connected to the sliding hook 32 for actuating the sliding hook.

Another important aspect of the pusher bar (or actuating element) 70 is that as the pusher bar 70 reciprocates vertically along the longitudinal axis of the pusher bar, the pusher bar engages a first bevel gear wheel 98 disposed above the gear box 72 in the housing 40 for actuating the rotator 62 (FIG. 1). More specifically, a second bevel gear wheel 100 (FIG. 1) of the rotator 62 is rotated by the first bevel gear wheel 98 when the first rack gear 76 of the pusher bar (or actuating element) 70 reciprocates along the longitudinal axis of the pusher bar. As described in greater detail below, the rotations of the rotator 62 allow unfastening of the end cap 22 from the catheter 24.

Exemplary directions of respective gear motions are indicated by corresponding arrows in FIG. 4, but other directions of motions are contemplated depending on an arrangement of the components of the interface gear assembly 30. Other suitable types of gear components, such as spur gears, straight bevel gears, spiral bevel gears, worm gears, hypoid gears, helical gears, herringbone gears, and the like, are contemplated as known in the art. Also, although the pusher bar 70 having a rectangular, elongate rod shape is shown for illustration purposes, other suitable configurations for translating linear motion to transverse or rotational motion, using different pusher bars, such as a tilting lever, a turning lever, a switching lever, a push and pull lever, and the like, are also contemplated to suit different applications such elements are herein referred to as actuating element. Further, in the embodiment according to FIG. 4 as well as in all other embodiments, a motor 31 and a programmable electronic control unit 32*a* for controlling said motor can also be used for moving the cradle assembly 12. Here, the pusher bar may be omitted and the motor may drive the interface gear assembly (or other suitable gear assemblies, see above) in order to move the cradle assembly 12.

Referring now to FIGS. 4, 5 and 9, in a preferred embodiment, the pusher bar (or actuating element) 70 includes a first torsion spring 102 constructed and arranged for actuating a stopper 104 connected to the horizontal plate 36, such that the cradle assembly 12 sequentially transitions between the cap-off position, to the fluid-delivery position, and to the cap-on position. More specifically, one end 106 of the first torsion spring 102 is fixedly attached to the pusher bar 70, and an opposite free end 108 of the torsion spring extends transversely from the pusher bar (FIG. 4).

In a preferred embodiment, a support member 110 (FIG. 5) is attached to a rear surface 112 of the horizontal plate 36 for supporting the stopper 104 such that the stopper is pivotally attached and secured to the support member by a pivot pin 114. As attached, the stopper 104 may pivot about the pivot pin 114 when the free end 108 of the first torsion spring 102 engages and pulls downwardly a first finger 116 extending from the stopper 104 against the force of a second torsion spring 118 connected to the stopper. Other suitable pivotable connections for the stopper 104 are contemplated to suit different applications.

When the stopper 104 pivots about the pivot pin 114, a second finger 120 extending from an opposite side of the stopper releases the cradle assembly 12 so that the cradle assembly laterally shifts or slides to the left side along the horizontal plate 36. For achieving the lateral movement of the cradle assembly 12, it is preferred that upper and lower grooves 121, forming a track, are provided in the horizontal body 16 of the cradle assembly, such that the horizontal plate 36 engages with the corresponding grooves, and the cradle assembly slidably, laterally shifts or slides to the left or right sides within the grooves.

Figure 7:
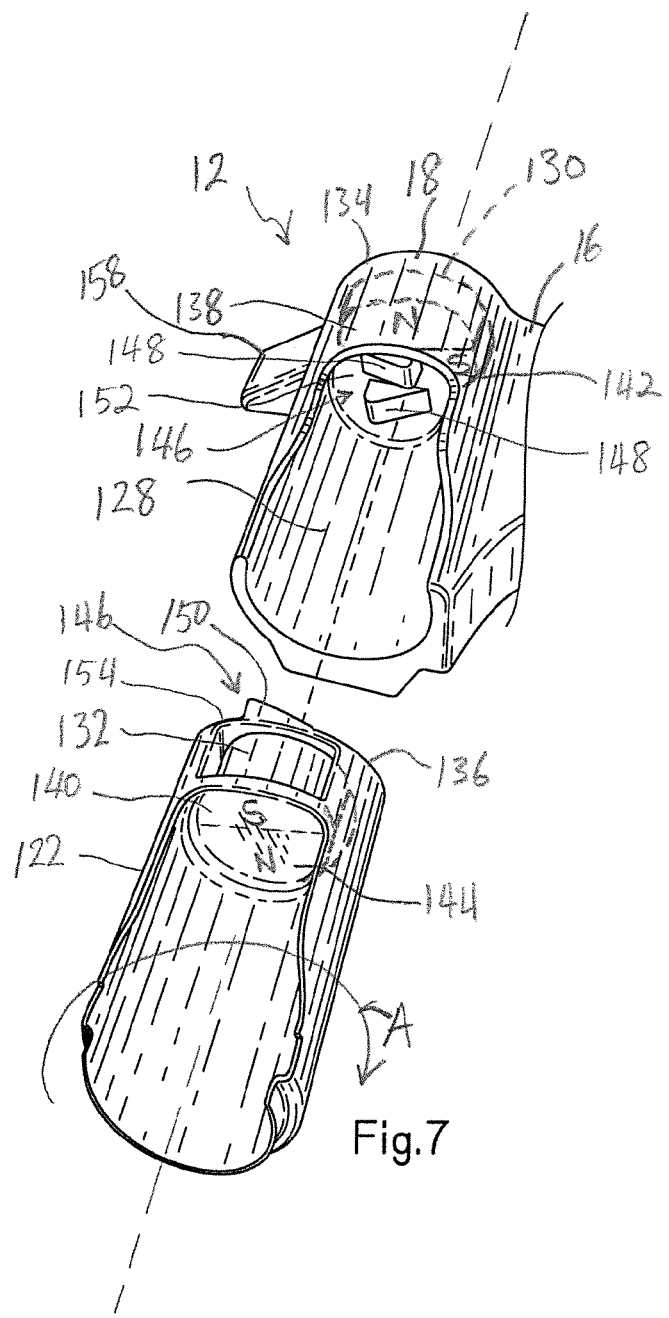
FIG. 7 is a partial exploded view of a first or left port of the movable cradle assembly of FIG. 1, featuring a magnetic cap sleeve.

Referring now to FIGS. 6, 6A, and 7-9, it is preferred that the first port 18 of the cradle assembly 12 has a first sleeve 122 (FIGS. 8 and 9) configured for receiving the end cap 22 of the catheter 24 (FIG. 9) to rotationally unfasten the end cap for replacement. Similarly, it is preferred that the second port 20 of the cradle assembly 12 has a second sleeve 124 (FIGS. 8 and 9) configured for receiving a replacement cap 126 (FIG. 9) to rotationally fasten the replacement cap on the catheter 24 after the dialysis therapy. Each sleeve 122, 124 is slidably insertable into a corresponding cavity 128 of the respective port 18, 20 such that the sleeves are freely movable and rotatable inside the cavity (FIGS. 6, 6A and 7).

An important aspect of the present apparatus 10 is that each port 18, 20 has a set of first and second port magnets 130, 132, wherein each port magnet is divided by opposing magnetic polarities. As an example only, it is contemplated that the first port magnet 130 is disposed on an upper end 134 of the first port 18, and the second port magnet 132 is disposed on a corresponding upper end 136 of the first sleeve 122. In one embodiment, the first port magnet 130 may assist the actuation of the cradle assembly 12 by using the magnetic fields of the magnets 38 (FIGS. 8 and 9) disposed near the opposite upper corners of the housing 40.

It is preferred that an upper half 138 of the first port magnet 130 and a corresponding upper half 140 of the second port magnet 132 have different magnetic polarities so that the first and second port magnets attract each other when the first and second port magnets are in a resting position. Similarly, a lower half 142 of the first port magnet 130 and a corresponding lower half 144 of the second port magnet 132 have different magnetic polarities so that the first and second port magnets attract each other when in the resting position.

For example, when the upper half 138 of the first port magnet 130 has a North polarity, the corresponding upper half 140 of the second port magnet 132 has a South polarity. Similarly, when the lower half 142 of the first port magnet 130 has the South polarity, the corresponding lower half 144 of the second port magnet 132 has the North polarity. Other suitable magnetic arrangements are contemplated to suit different applications.

Another important aspect of the present apparatus 10 is that each port 18, 20 has a one-way directional mechanism, generally designated 146, for rotating the corresponding sleeves 122, 124 in only one direction while preventing motion in the opposite direction during operation. For example, this one-way directional rotation of each sleeve 122, 124 is achieved by a set of complementary first and second one-directional teeth 148, 150. More specifically, at least one first one-directional tooth 148 is provided on an inner surface 152 of the upper end 134 of the first port 18, and at least one corresponding second one-directional tooth 150 is provided on an outer surface 154 of the upper end 136 of the first sleeve 122 in a complementary relationship with the first one-directional tooth 148.

Figure 8:
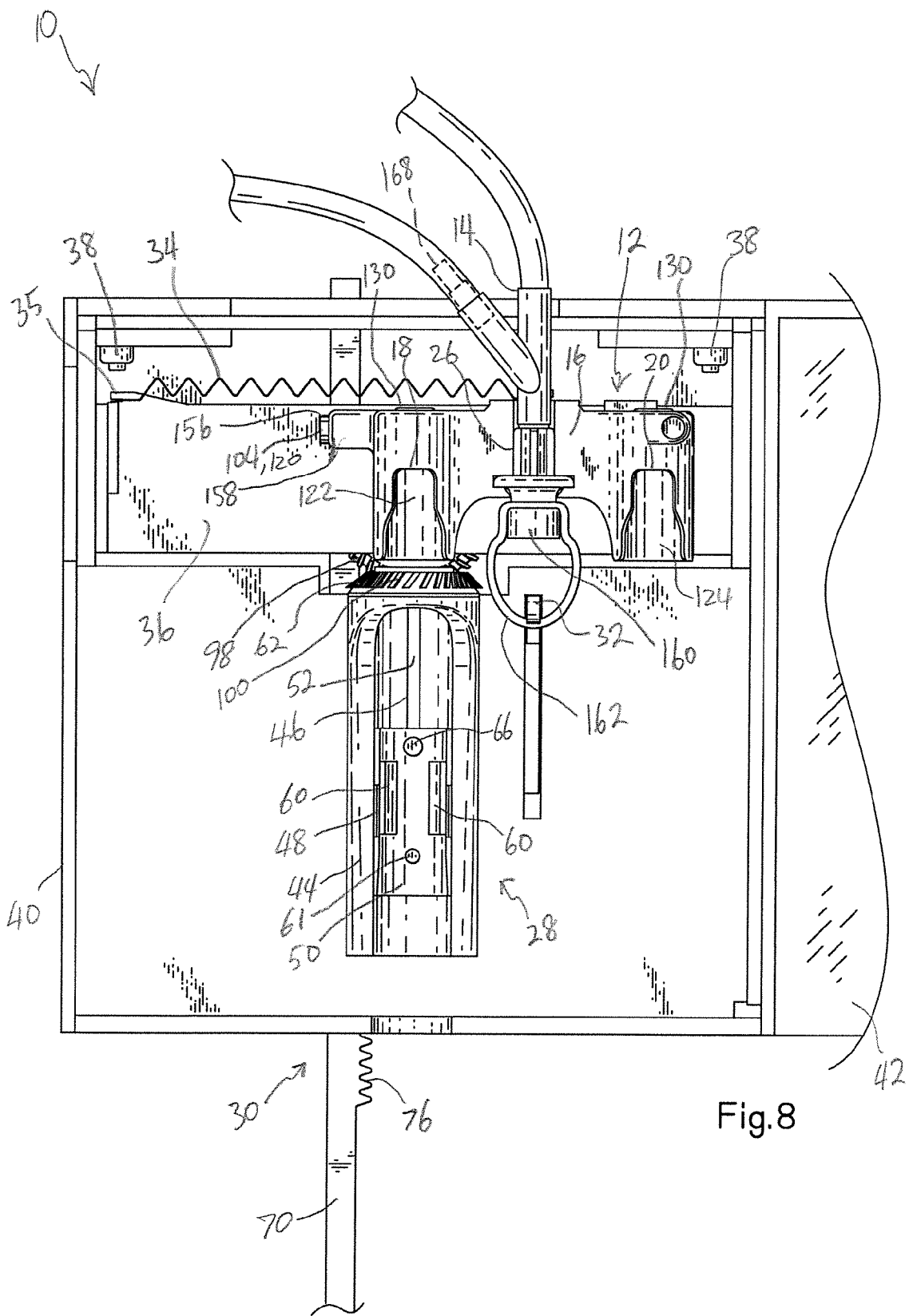
FIG. 8 is a plan view of the present apparatus of FIG. 1 after insertion of a fluid bag connector into a connector holder of the cradle assembly.

As such, the first and second one-directional teeth 148, 150 are arranged in a cooperative relationship resembling a ratchet and pawl mechanism. For example, the first sleeve 122 freely rotates clockwise only, relative to the longitudinal axis of the first sleeve as indicated by an arrow A (FIG. 7) while the end cap 22 held in the first sleeve is rotated in the same clockwise direction via the rotator 62 (FIGS. 8 and 9). Conversely, as is the case with the first sleeve 122, the second sleeve 124 freely rotates counterclockwise only, relative to the longitudinal axis of the second sleeve while the replacement cap 126 held in the second sleeve is rotated by the rotator 62.

More specifically, due to a particular geometric shape of the first and second one-directional teeth 148, 150, only the clockwise rotation of the first sleeve 122 is allowed, but a counterclockwise rotation of the first sleeve is prevented by the corresponding second one-directional teeth 150 when the end cap 22 is rotated in the counterclockwise direction via the rotator 62. Conversely, only the counterclockwise rotation of the second sleeve 124 is allowed, but the clockwise rotation of the second sleeve is prevented by the corresponding second one-directional teeth 150. Other suitable geometric shapes of the first and second one-directional teeth 148, 150 are contemplated.

As shown in FIGS. 6 and 6A, to provide opposite locking operations for the first and second ports 18, 20, it is preferred that the first and second one-directional teeth 148, 150 are arranged in an opposite orientation (FIGS. 6 and 6A) for the first and second sleeves 122, 124. As a result, while the first sleeve 122 is used for unfastening of the end cap 22 from the catheter 24, the second sleeve 124 is used for fastening of the replacement cap 126 onto the catheter. In FIG. 6A, corresponding components of the second port 20 are indicated with reference numbers with a prime (') designation.

Referring now to FIGS. 5, 7, and 8, the cradle assembly 12 is initially positioned in the cap-off position (FIG. 8) by sliding the cradle assembly to the right side along the horizontal plate 36 against the force of the tension element 34 until the second finger 120 of the stopper 104 is inserted into a bore 156 disposed on the horizontal plate under the action of the second torsion spring 118. At that moment, a portion of the second finger 120 of the stopper 104 protrudes out of the bore 156 to abut against a leftmost edge 158 of the cradle assembly 12, thereby positioning the cradle assembly in the cap-off position.

Referring now to FIGS. 8 and 9, in a preferred embodiment, the fluid bag connector 14 is securely closed with a valve cover 160 having an elastic pull strap 162. In preparation of the dialysis therapy, the fluid bag connector 14 is securely inserted into the connector holder 26, and the pull strap 162 is connected to the sliding hook 32 for subsequent removal of the valve cover 160. The catheter 24 having the end cap 22 is inserted into the slider 50 of the catheter holder assembly 28, and the replacement cap 126 is inserted into the second sleeve 124 of the second port 20. As discussed above, the indent portions 58 of the catheter 24 are securely wrapped around or held by the inner protrusions 60 of the slider 50 for preventing unwanted rotational movement of the catheter. Further, the stop magnets 61 magnetically hold the slider 50 within the body 44 of the catheter holder assembly 28. Further, as indicated in FIG. 9, the apparatus 10 may comprise a radiation source 33 (e.g. an ultraviolet light source) for achieving an antibacterial effect. Opposite the radiation source 33 or at any other suitable place, a reflective surface 34a for reflecting the radiation emitted by the radiation source 33 may be provided. Such a radiation source 33 and reflective surface(s) 34a may also be provided in any other embodiment described herein.

Referring now to FIGS. 3-5 and 10, the cover 42 is closed, and the pusher bar (or actuating element) 70 is pushed upwardly toward the catheter holder assembly 28 as indicated by an arrow B. As the pusher bar 70 travels upwardly with the slider mover 56, the catheter 24 held by the slider 50 is moved upwardly toward the first port 18, such that the first sleeve 122 receives the end cap 22 of the catheter and secures the end cap in the first sleeve by an annular friction fit. Also, when the slider 50 reaches the rotator 62, the slider is magnetically coupled to the rotator under the magnetic force of the rotator magnets 64 and the corresponding slider magnets 66.

During the upward movement of the pusher bar 70, the free end 108 of the first torsion spring 102 is bent by the first finger 116 of the stopper 104 without rotating the stopper against the force of the second torsion spring 118. At approximately the same time, the third rack gear 96 moves downwardly away from the cradle assembly 12, and the sliding hook 32 connected to the third rack gear pulls the elastic pull strap 162, thereby removing the valve cover 160 from the fluid bag connector 14. The valve cover 160 is secured to the connector 14 by a friction fit. As the pusher bar 70 further travels upwardly, the first rack gear 76 on the pusher bar rotates the first bevel gear wheel 98, which in turn rotates the second bevel gear wheel 100 of the rotator 62, such that the first sleeve 122 and the slider 50 magnetically coupled to the rotator are simultaneously rotated in the clockwise direction indicated by an arrow C along with the catheter 24.

As discussed above, the first port magnet 130 on the upper end 134 of the first port 18 and the second port magnet 132 on the upper end 136 of the first sleeve 122 generate a magnetic attracting force between each other in the resting position. However, when the first sleeve 122 is rotated in the clockwise direction as described above, since the first port magnet 130 is stationary in the upper end 134 of the first port 18, only the second port magnet 132 of the first sleeve 122 is rotated along with the first sleeve. As a result, the first and second port magnets 130, 132 generate a magnetic repelling force due to the opposing magnetic polarities between the first and second port magnets. Because the first sleeve 122 securely holds the end cap 22 being fastened to the catheter 24, a current position of the first sleeve is maintained against the magnetic repelling force.

Referring now to FIGS. 3-5, 7, 11, and 12, the pusher bar (or actuating element) 70 is pulled downwardly away from the cradle assembly 12 as indicated by an arrow D. As the pusher bar 70 travels downwardly, the pusher bar rotates in a reverse direction the first bevel gear wheel 98, which in turn rotates the second bevel gear wheel 100 of the rotator 62, such that only the slider 50 is rotated in the counterclockwise direction indicated by an arrow E along with the catheter 24. Since the first sleeve 122 is prevented from turning in the counterclockwise direction due to the one-way directional mechanism 146 (FIG. 7) of the first port 18, the end cap 22 of the catheter 24 prevented from rotating and being held by the first sleeve is unfastened by the rotating action of the slider 50.

After separating the end cap 22 from the catheter 24, the first sleeve 122 is pushed away from the upper end 134 of the first port 18 under the action of the magnetic repelling force between the first and second port magnets 130, 132. This causes the first sleeve 122 to be released from the one-way directional mechanism 146, and the first sleeve is automatically rotated in the counterclockwise direction under the magnetic attracting force of the first and second port magnets 130, 132, thereby returning the first sleeve to the resting position.

During the downward movement of the pusher bar 70, the free end 108 of the first torsion spring 102 engages the first finger 116 of the stopper 104, thereby rotating the stopper against the force of the second torsion spring 118. Consequently, the second finger 120 of the stopper 104 is extracted from the bore 156 of the horizontal plate 36, and the cradle assembly 12 is shifted laterally to the left side along the horizontal plate 36 under the action of the return spring 34 until the second finger is engaged by an indent region 164 (FIG. 12) of the body 16 of the cradle assembly. As the pusher bar 70 further travels downwardly, the slider 50 is moved downwardly by the slider mover 56, decoupled from the rotator 62, and magnetically held by the attracting force of the two stop magnets 61 of the slider and the body 44 of the catheter holder assembly 28.

Figure 11:
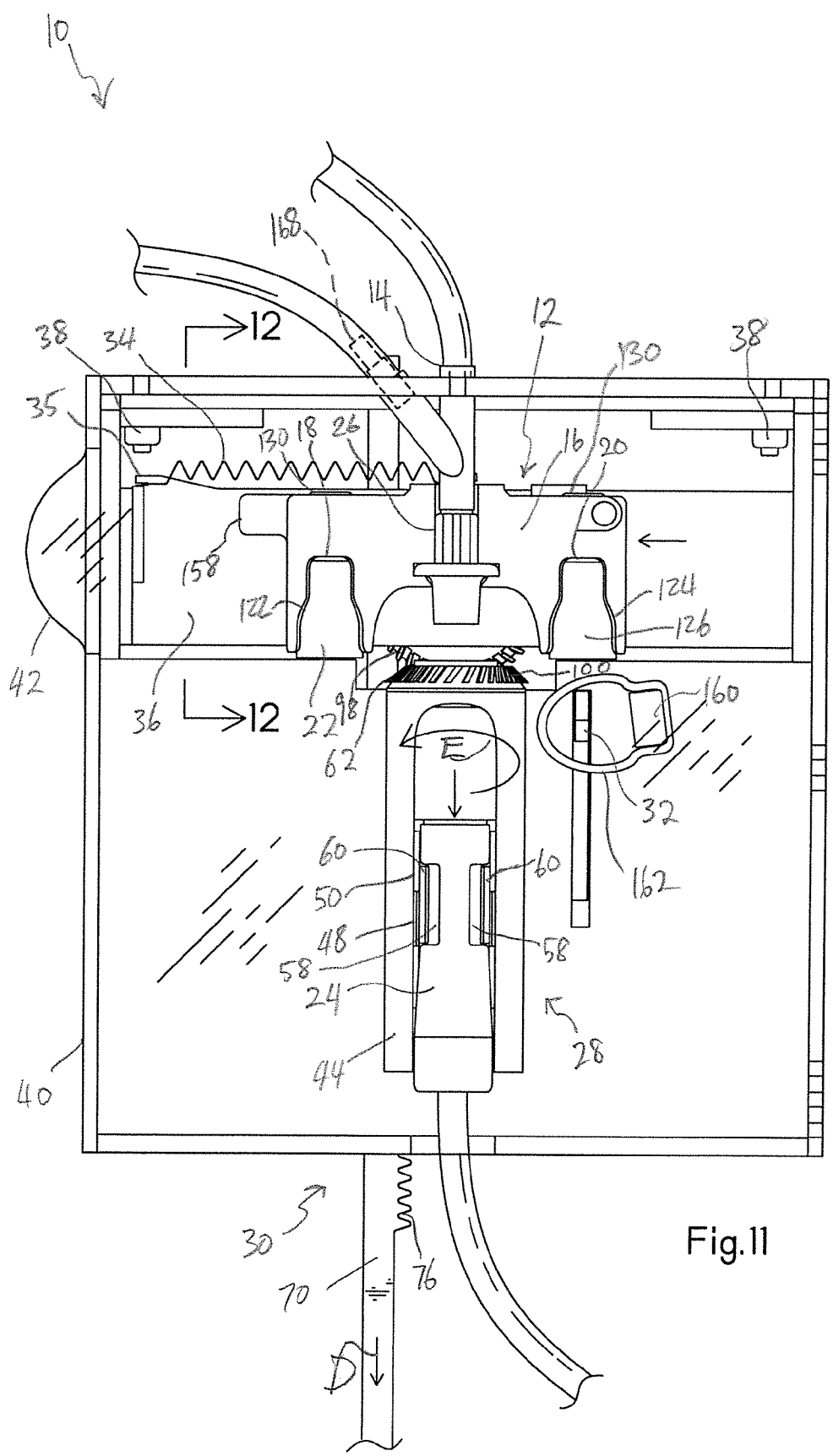
FIG. 11 is a plan view of the present apparatus of FIG. 10, featuring the movable cradle assembly in a fluid-delivery position after removal of the catheter from the first port of the cradle assembly.

At that moment, the cradle assembly 12 is positioned in the fluid-delivery position. The fluid-delivery position refers to a second position in which the connector holder 26 of the cradle assembly 12 is substantially longitudinally aligned with the catheter holder assembly 28 so that the catheter 24 is ready to be connected to the fluid bag connector 14 for receiving medicinal fluid (FIG. 11). As the pusher bar 70 further travels downwardly, the catheter 24 without the end cap 22 is lowered and ready for connection to the fluid bag connector 14 in the connector holder 26.

Referring now to FIGS. 3-5, 12, and 13, the pusher bar (or actuating element) 70 is again pushed upwardly toward the cradle assembly 12 as indicated by an arrow F. As the pusher bar 70 travels upwardly with the slider mover 56, the catheter 24 held by the slider 50 is moved upwardly toward the fluid bag connector 14. When the slider 50 reaches the rotator 62, the slider is again magnetically coupled to the rotator under the magnetic force of the rotator magnets 64 and the corresponding slider magnets 66.

During the upward movement of the pusher bar 70, the free end 108 of the first torsion spring 102 is bent by a third finger 166 (FIG. 12) of the stopper 104 without further rotating the stopper against the force of the second torsion spring 118. At this point, the second finger 120 is still engaged by the indent region 164 of the cradle assembly 12 under the action of the return spring 34, maintaining the cradle assembly in the fluid-delivery position.

As the pusher bar 70 further travels upwardly, the pusher bar rotates the first bevel gear wheel 98, which in turn rotates the second bevel gear wheel 100 of the rotator 62, such that the slider 50 magnetically coupled to the rotator is rotated in the clockwise direction indicated by an arrow G along with the catheter 24 to be threadably and fluidly connected to the fluid bag connector 14. After the connection of the catheter 24 to the fluid bag connector 14 in this manner, a frangible inline seal 168 of the fluid bag connector can be broken for receiving the medicinal fluid from a fluid bag (not shown) for the dialysis therapy.

Referring now to FIGS. 3-5, 12, and 14, after completion of the dialysis therapy, the pusher bar (or actuating element) 70 is again pulled downwardly away from the cradle assembly 12 as indicated by an arrow H. As the pusher bar 70 travels downwardly, the pusher bar rotates in the reverse direction the first bevel gear wheel 98, which in turn rotates the second bevel gear wheel 100 of the rotator 62, such that the slider 50 is rotated in the counterclockwise direction indicated by an arrow I along with the catheter 24.

During the downward movement of the pusher bar 70, the free end 108 of the first torsion spring 102 engages the third finger 166 of the stopper 104, thereby rotating the stopper against the force of the second torsion spring 118. Consequently, the second finger 120 of the stopper 104 is extracted from the indent region 164 of the cradle assembly 12, and the cradle assembly is shifted laterally to the left side along the horizontal plate 36 under the action of the return spring 34 until the leftmost edge 158 of the cradle assembly abuts a left sidewall 170 (FIG. 14) of the housing 40. As the pusher bar 70 further travels downwardly, the slider 50 is moved downwardly by the slider mover 56, decoupled from the rotator 62, and magnetically held by the attracting force of the two stop magnets 61 of the slider and the body 44 of the catheter holder assembly 28.

At that moment, the cradle assembly 12 is positioned in the cap-on position. The cap-on position refers to a third position in which the second port 20 of the cradle assembly 12 is substantially longitudinally aligned with the catheter holder assembly 28 so that the catheter 24 is ready to be connected to the replacement cap 126. As the pusher bar 70 further travels downwardly, the catheter 24 is lowered and ready for connection to the replacement cap 126 in the second port 20.

Referring now to FIGS. 3-5, 12, and 15, the pusher bar (or actuating element) 70 is again pushed upwardly toward the cradle assembly 12 as indicated by an arrow J. As the pusher bar 70 travels upwardly with the slider mover 56, the catheter 24 held by the slider 50 is moved upwardly toward the second port 20. When the slider 50 reaches the rotator 62, the slider is again magnetically coupled to the rotator under the magnetic force of the rotator magnets 64 and the corresponding slider magnets 66.

Figure 12:
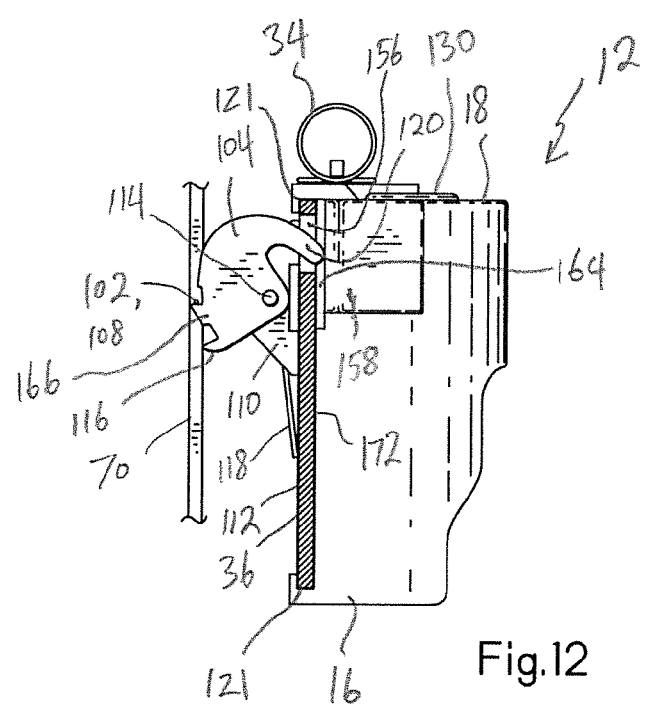
FIG. 12 is a cross-section of the movable cradle assembly between the cap-off and fluid-delivery positions taken along the line 12-12 of FIG. 11 and in the direction generally indicated.
Figure 13:
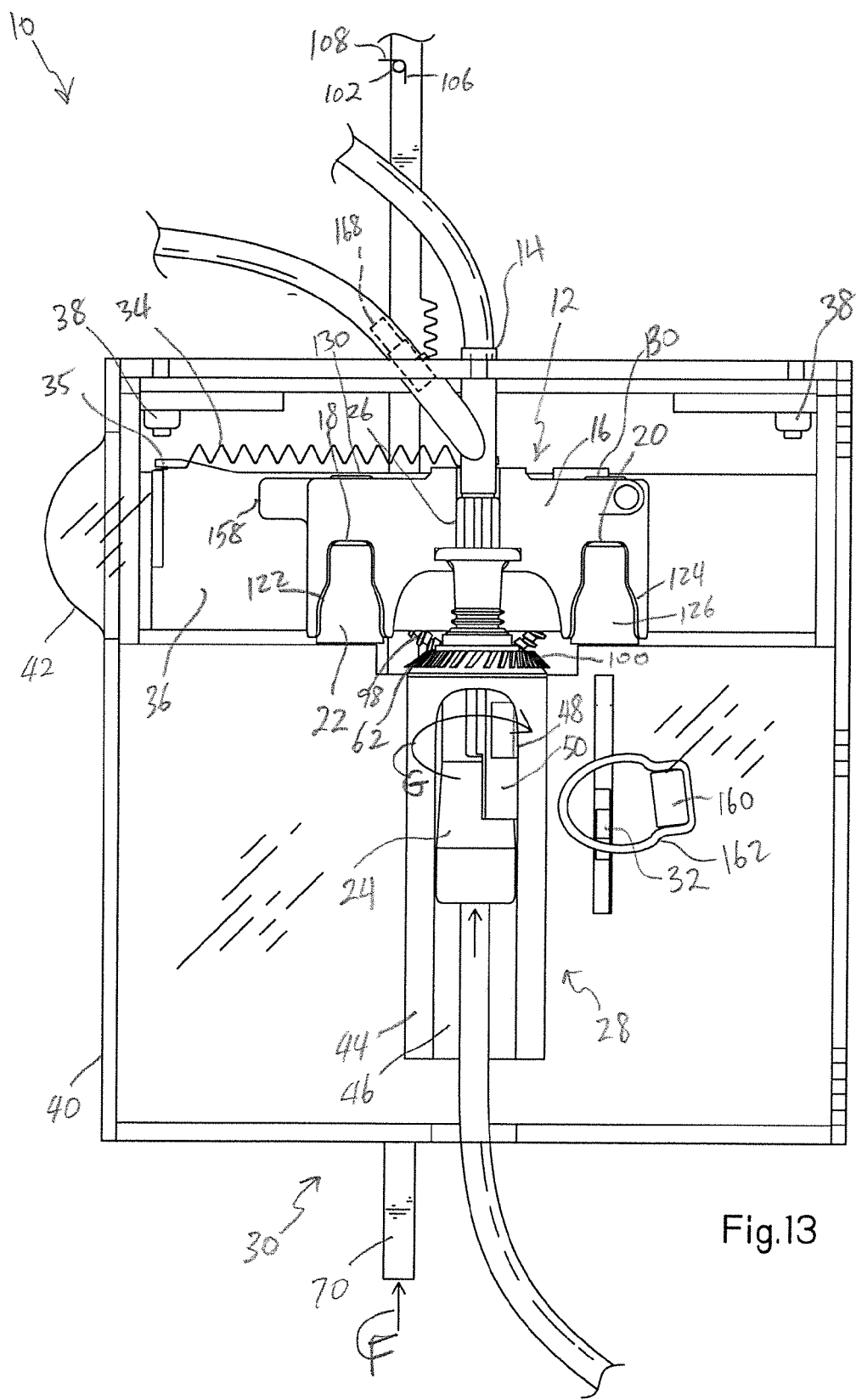
FIG. 13 is a plan view of the present apparatus of FIG. 12 after insertion of the catheter towards the cradle assembly and connection with the fluid bag connector.
Figure 14:
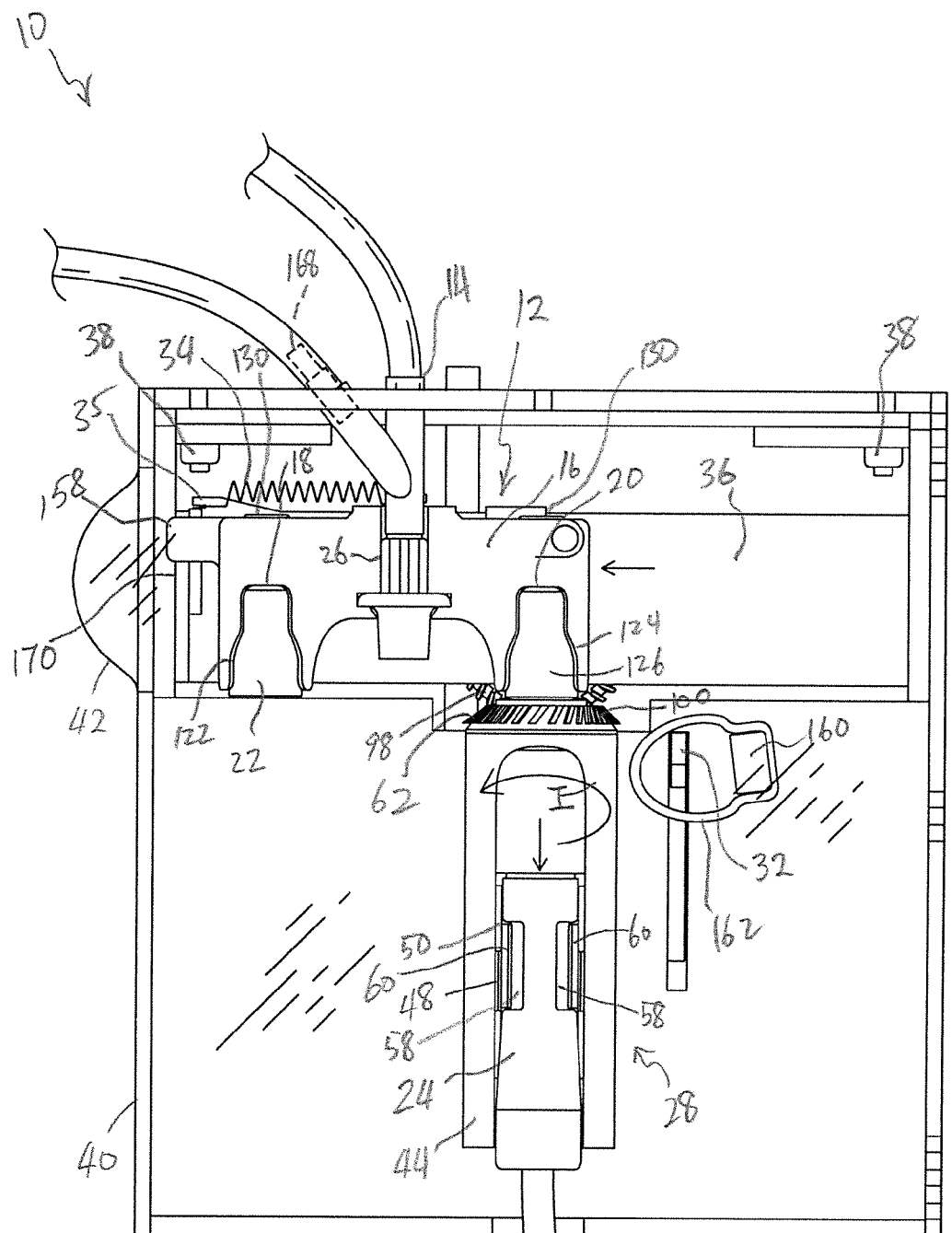
FIG. 14 is a plan view of the present apparatus of FIG. 13, featuring the movable cradle assembly in a cap-on position after disconnection and removal of the catheter from the fluid bag connector.
Figure 15:
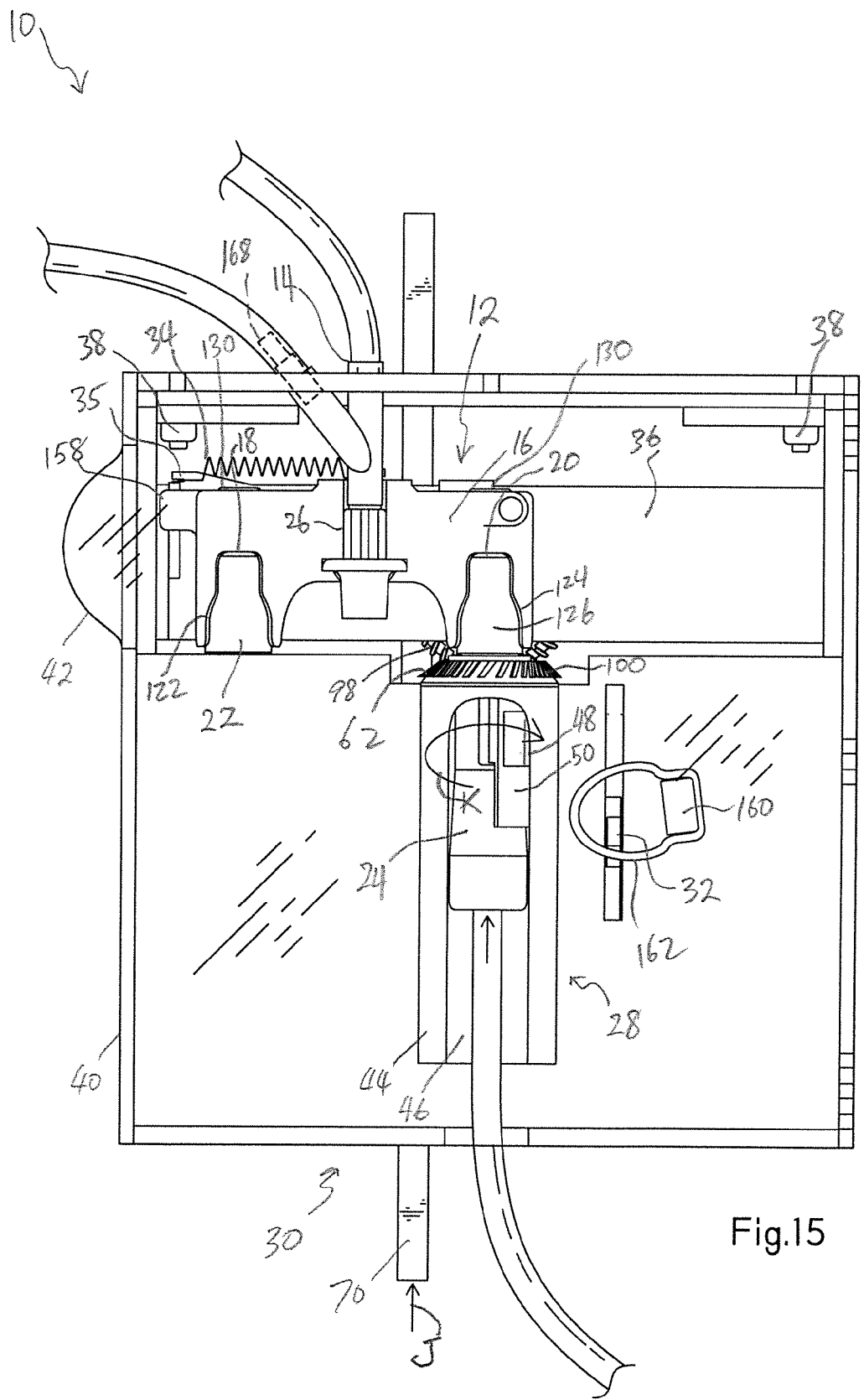
FIG. 15 is a plan view of the present apparatus of FIG. 14 after insertion of the catheter into a second or right port of the movable cradle assembly.
Figure 16:
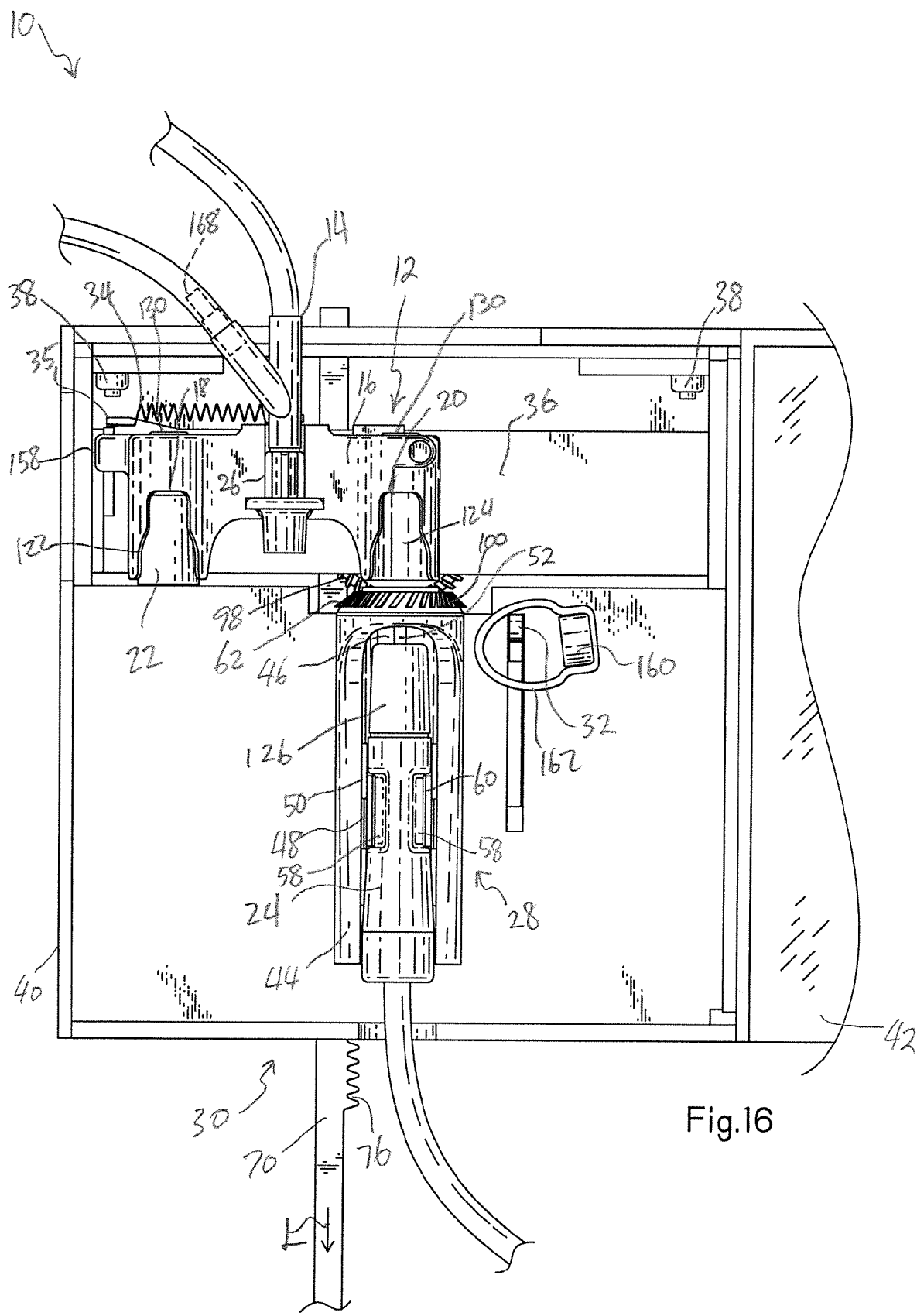
FIG. 16 is a plan view of the present apparatus of FIG. 15 after removal of the catheter from the second port of the movable cradle assembly.

During the upward movement of the pusher bar 70, the free end 108 of the first torsion spring 102 passes by (or is bent by) the stopper 104 without rotating the stopper (FIG. 12). Although the second finger 120 of the stopper 104 is extracted from the indent region 164 of the cradle assembly 12 for establishing the cap-on position, the second finger continues to engage a rear surface 172 of the horizontal body 16 of the cradle assembly under the action of the second torsion spring 118 during the cap-on position.

As the pusher bar 70 further travels upwardly, the pusher bar rotates the first bevel gear wheel 98, which in turn rotates the second bevel gear wheel 100 of the rotator 62, such that the slider 50 magnetically coupled to the rotator is rotated in the clockwise direction indicated by an arrow K along with the catheter 24 to be connected to the replacement cap 126. Unlike the first sleeve 122, since the second sleeve 124 is prevented from turning in the clockwise direction due to the one-way directional mechanism 146 of the second port 20, the replacement cap 126 held by the second sleeve is fastened by the rotating action of the slider 50.

Referring now to FIGS. 3-5 and 16, after fastening the replacement cap 126 onto the catheter 24, the pusher bar 70 is pulled downwardly away from the cradle assembly 12 as indicated by an arrow L. As the pusher bar 70 travels downwardly, the pusher bar rotates the first bevel gear wheel 98, which in turn rotates the second bevel gear wheel 100 of the rotator 62, such that the slider 50 is rotated in the counterclockwise direction. Since the catheter 24 is held by the slider 50 and the replacement cap 126 is fastened to the catheter, the replacement cap and the second sleeve turn together in the counterclockwise direction. As the pusher bar 70 further travels downwardly, the slider 50 is moved downwardly by the slider mover 56, decoupled from the rotator 62, and the replacement cap 126 is separated from the second port 20.

After separating the replacement cap 126 from the second port 20, the second sleeve 124 is pushed away from the upper end 134' (FIG. 6A) of the second port under the action of the magnetic repelling force between the first and second port magnets 130, 132. This causes the second sleeve 124 to be released from the one-way directional mechanism 146', and the second sleeve is automatically rotated in the clockwise direction under the magnetic attracting force of the first and second port magnets 130, 132, thereby returning the second sleeve in the resting position.

Subsequently, the slider 50 is magnetically held by the attracting force of the two stop magnets 61 of the slider and the body 44 of the catheter holder assembly 28. The cover 42 is opened, and the catheter 24 having the replacement cap 126 is pulled out of the catheter holder assembly 28 for storage. To initialize the present apparatus 10, the cradle assembly 12 can be shifted to the right side along the horizontal plate 36 against the force of the tension element 34 until the second finger 120 of the stopper 104 is inserted again into the bore 156 under the action of the second torsion spring 118, thereby locking and positioning the cradle assembly 12 in the cap-off position.

Figure 17:
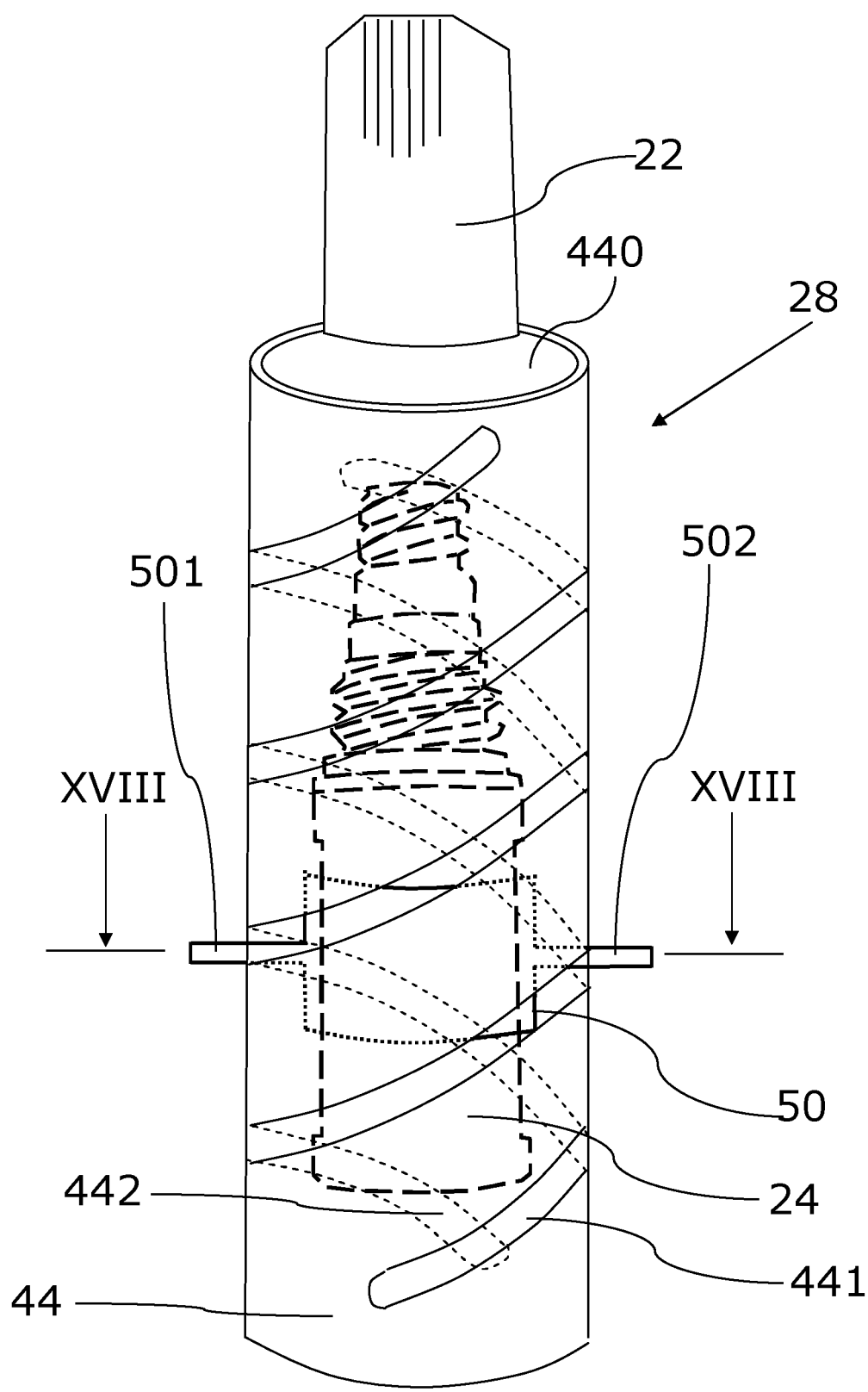
FIG. 17 is a schematical view of yet another embodiment or aspect of the apparatus according to the present invention.
Figure 18:
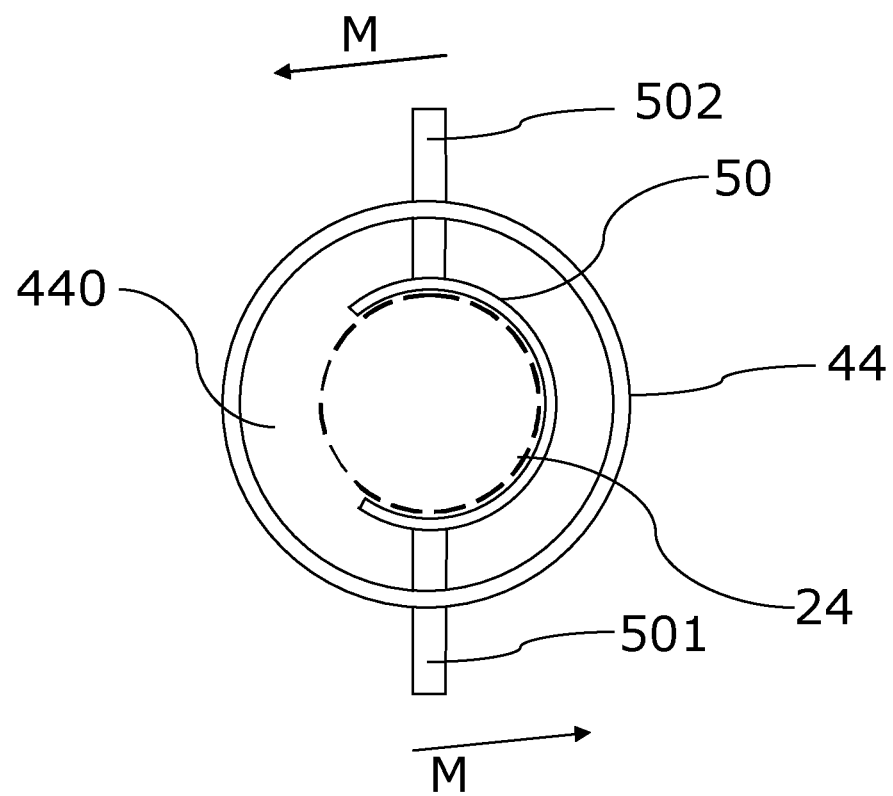
FIG. 18 is a cross sectional view of the apparatus of FIG. 17.

Now FIGS. 17 and 18 show yet another embodiment of the holder assembly 28 or cylindrical body 44 that may be alternatively used in all embodiments or aspects of the present invention. Here, the (e,g, hollow) cylindrical body 44 comprises an opening 440 enclosed by a circumferential wall of the body 44 for receiving the tubular fitting (e.g. catheter), and a slider 50 arranged in said opening 440 of said body 44, wherein said slider 50 is configured to hold said tubular fitting (e.g. catheter) 24 such that the latter can be carried by said slider 50 within said body 44.

For guiding a movement of the slider 50 and tubular fitting 24 held by the slider 50 (e.g. in a form-fitting and/or force-fitting manner) said cylindrical body 44 comprises a guiding means 441, 442 which is formed as two opposing helical slots 441, 442 formed in the cylinder body 44 (e.g. in its wall) with which slots 441, 442 the slider 50 engages. For this, the slider 50 may comprise two pins 501, 502, wherein each pin 501, 502 engages with an associated slot 441, 442 and may protrude radially out of the respective slot 441, 442. Thus, when the slider 50 (and thus the tubular fitting 24 fastened to the slider 50) translates in the longitudinal direction of the cylindrical body 44 (i.e. along its cylinder axis) it rotates simultaneously which allows to fasten or unfasten the end cap 22 of the tubular fitting 24 depending on the translation direction. Specifically, in case the pins 501, 502 and slider 50 are rotated clock-wise, the slider 50 and fitting 24 rotate clock-wise in direction M (cf. FIG. 18) and move towards cap 22 such that the fitting is rotationally fastened to end cap 22. Here, end cap 22 may be hold by some suitable cap holder, for instance a left and right port 18, 20 as described herein.

Further, said pins 501, 502 may be coupled to a means for driving said slider 50 and particularly for moving the cap holders (e.g. an interface gear assembly as describe herein) or other suitable means. Further, the present embodiment may be used with a cradle assembly 12 as described herein or with other suitable means for fastening and unfastening an end cap 22 to the fitting 24 and for connecting it to a connector 14 (e.g. fluid bag connector).

Further, particularly, in all of the afore-described embodiments and aspects of the present invention, the cradle assembly 12 and/or the cylindrical body 44 (and particularly components connected thereto) may be releasably connected to a housing (e.g. 40) of the apparatus 10 or to the apparatus 10 such that these components can be removed from said housing 40 or from the apparatus 10, particularly when the cradle assembly 12 is in the second position and/or when the fitting 24 is connected to the connector (e.g. fluid bag connector) 14. This has e.g. the benefit that a patient does not have to carry the housing as well when having the fitting 24 (e.g. catheter) and connector 14 in fluid connection during fluid-delivery.

While a particular embodiment of the present connecting apparatus has been described herein, it will be appreciated by those skilled in the art that changes and modifications may be made thereto without departing from the present disclosure in its broader aspects, and as set forth in the following claims.

Figure 24:
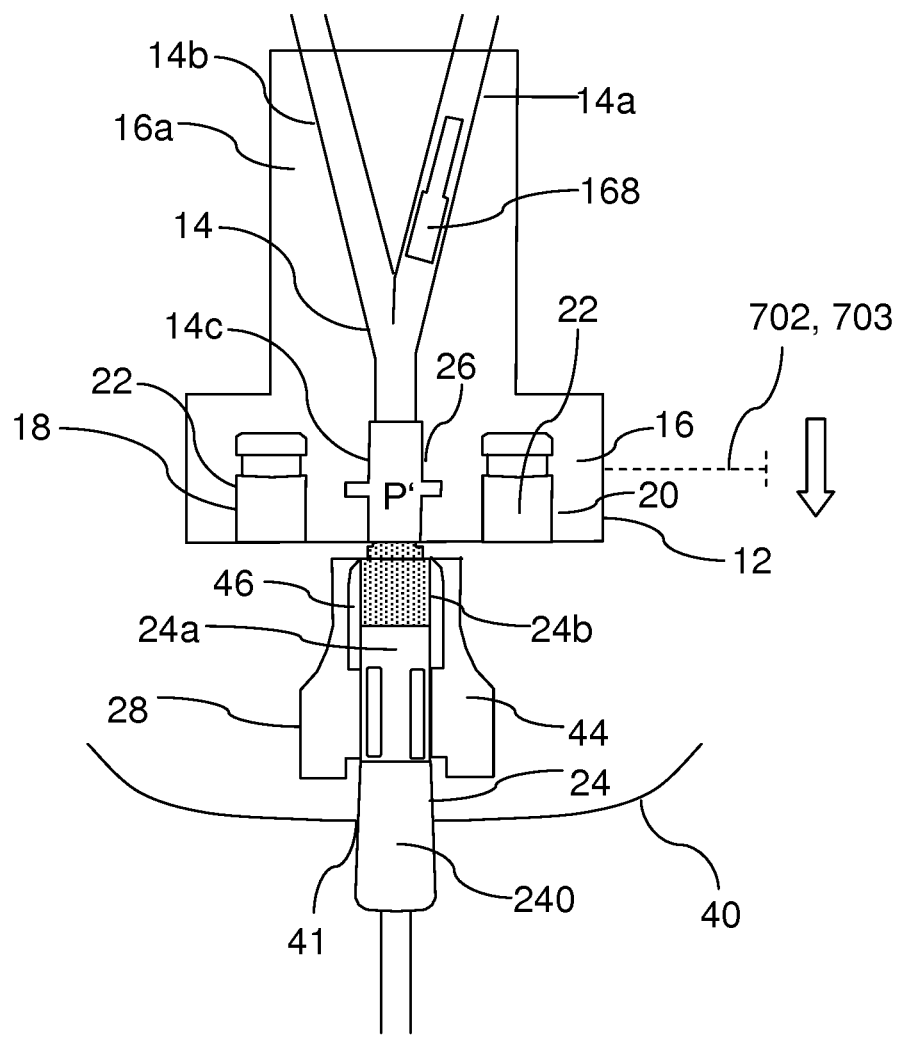
Figure 25:
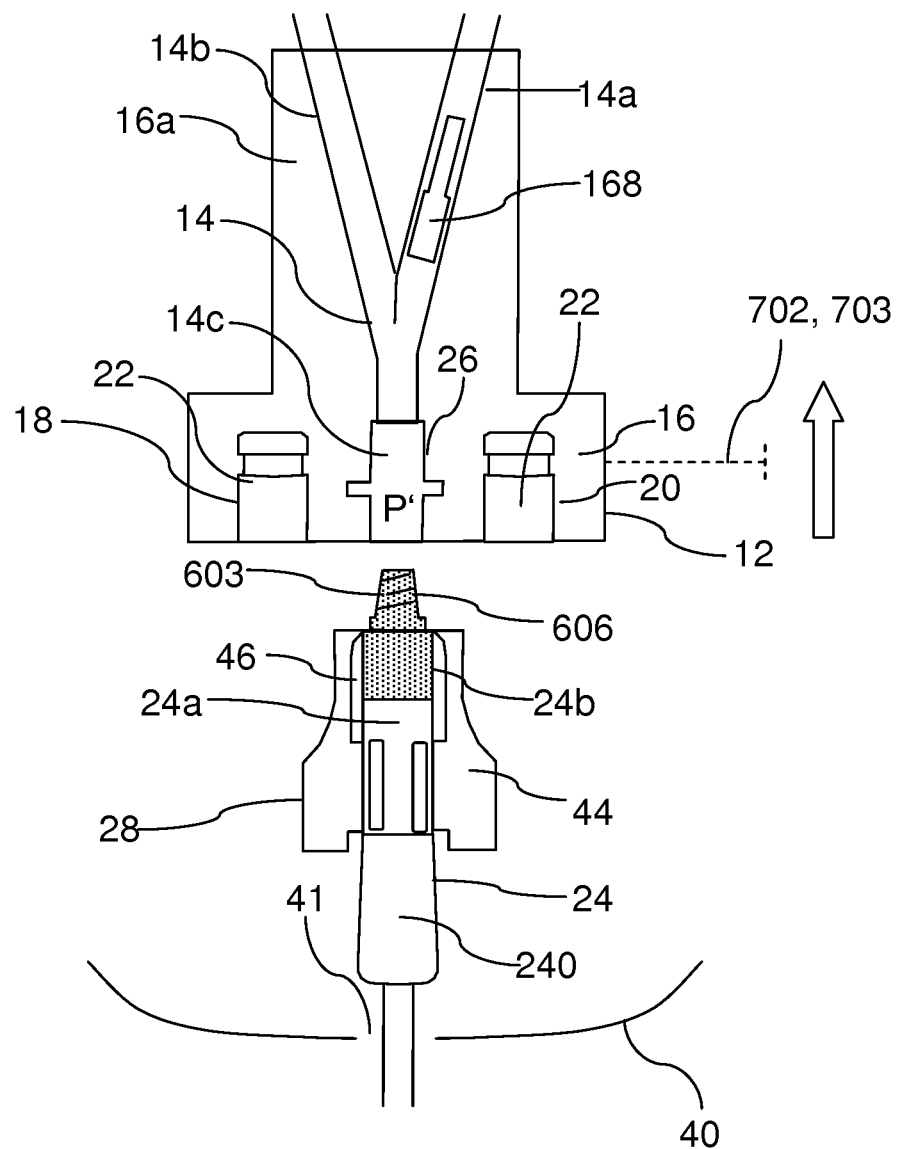
Figure 26:
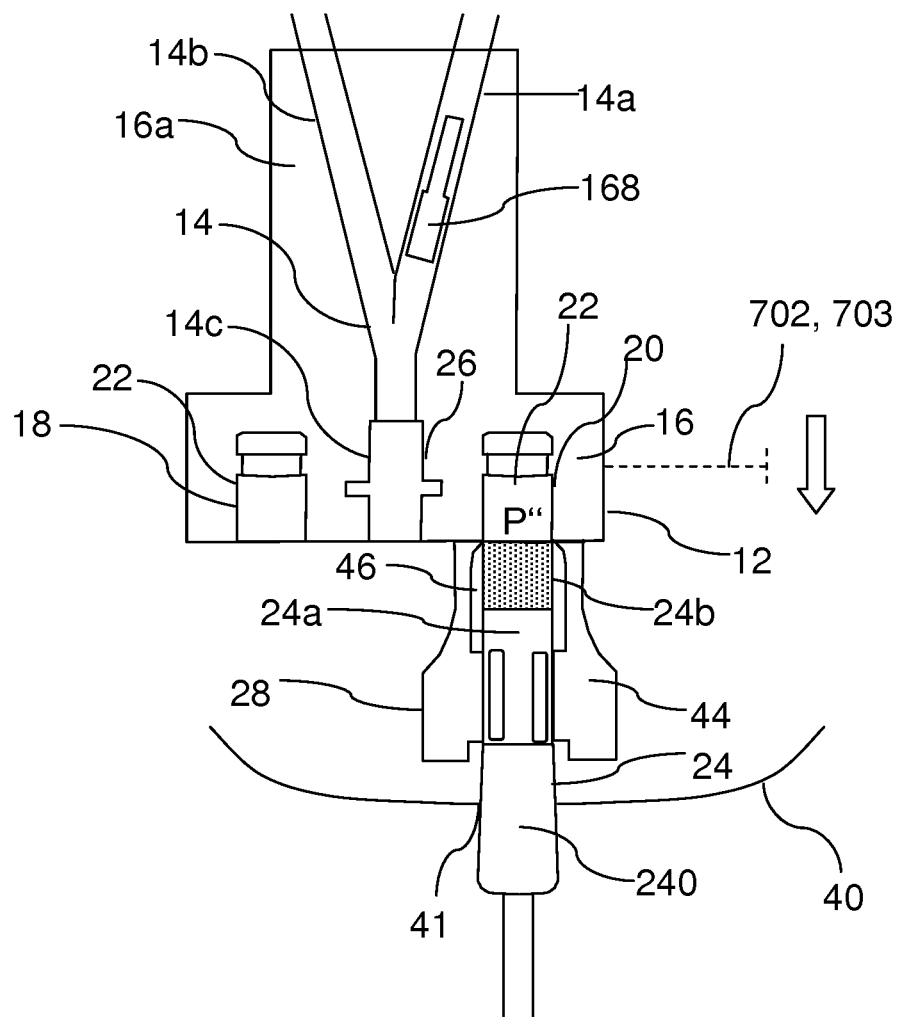

FIGS. 19 to 26 show a further embodiment of an apparatus 10 according to the invention for connecting and disconnecting a tubular fitting 24 to a connector 14, wherein the apparatus 10 comprises a cradle assembly 12 configured for accommodating the connector 14, the cradle assembly 12 including a body 16 having: a first port 18 and a second port 20, said first and second ports being disposed at opposite ends of said body 16, each said port 18, 20 configured for receiving an end cap 22 of the tubular fitting 24 to fasten or unfasten the end cap 22 for replacement by a plugging (fasten) or pulling (unfasten) movement, and a connector holder 26 being disposed between said first and second ports 18, 20, and configured for accommodating insertion of the connector 14; a holder assembly 28 configured for accommodating insertion of the tubular fitting 24; and a means 30 configured for operating said cradle assembly 12 and said holder assembly 28, particularly via an actuating means 702 that may comprise a handle 703 that is accessible from outside a housing 42 of the apparatus 10 (cf. FIGS. 22 to 26) so that said cradle assembly 12 is reciprocable (or can be moved back and forth) in a transverse direction relative to said holder assembly 28 between a first position P (cf. FIGS. 22 and 23), a second position P' (cf. FIGS. 24 and 25), and a third position P''' (cf. FIG. 26). In all embodiments the cradle assembly 12 (and particularly also holder assembly 28) may be guided by a guiding means 700 (see also below) and said means 30 may be configured to e.g. mechanically transform a force on an actuating element 702 comprising particularly a handle for manual actuation of a user into a linear movement of the cradle assembly (and particularly holder assembly) between the positions P, P', and P'''. Means 30 may also comprise a drive such as an (e.g. electrical) motor 31, particularly for moving the cradle assembly 12 between said positions P, P', P'''. The actuating element 702, 703 may then be configured for triggering said drive. Further, the movement of the holder assembly 28 described herein may be achieved by mechanically coupling holder assembly 28 to the cradle assembly 12. Further, the holder assembly may also be driven by said drive/motor 31. Particularly, the drive or motor 31 may be configured to be controlled by an electronic control unit 32a (as indicated for example in FIG. 21). By means of this drive/motor 31 and control unit 32a, the movement of the cradle assembly 12 and particularly of the holder assembly 28 can be programmed in beforehand (e.g. by uploading a corresponding software) so that the movement of the cradle assembly 12 (and particularly of the holder assembly 28) between the individual positions can be carried out automatically.

Figure 19:
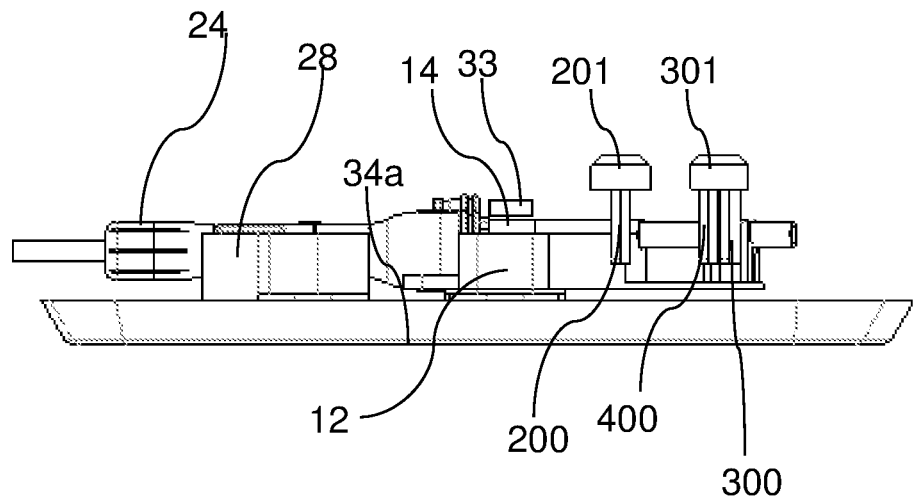
FIG. 19 is a lateral view of a further embodiment of an apparatus according to the invention.
Figure 20:
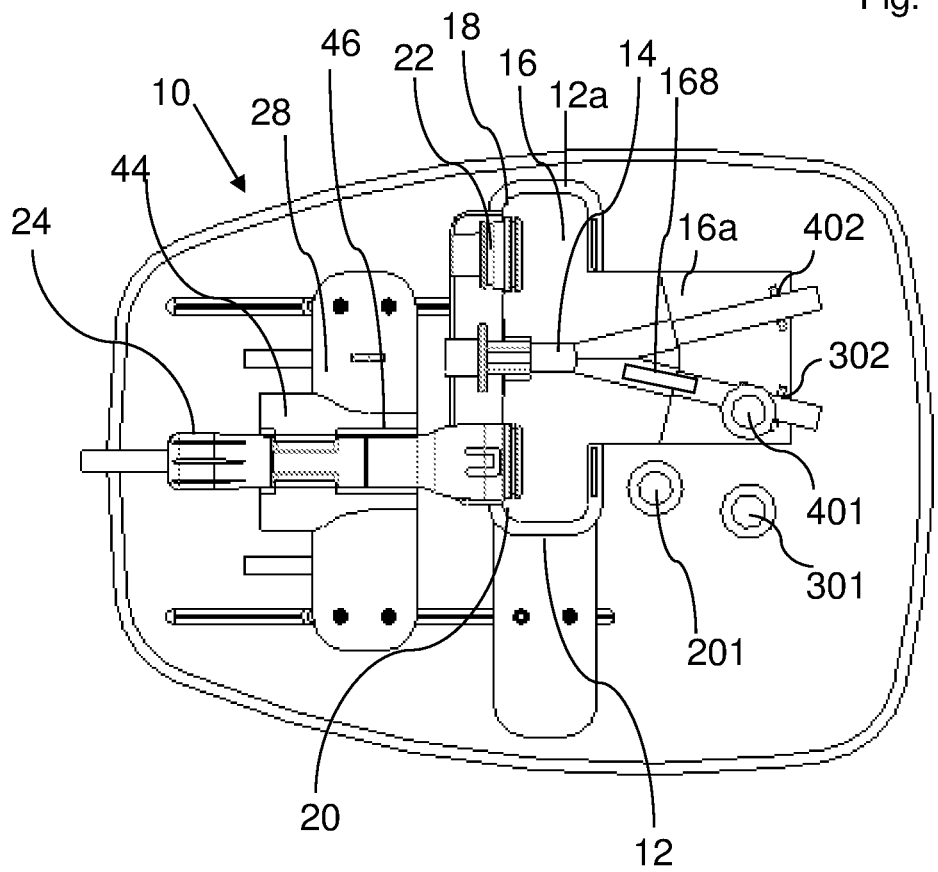
FIG. 20 is a plan view of the apparatus of FIG. 19.
Figure 21:
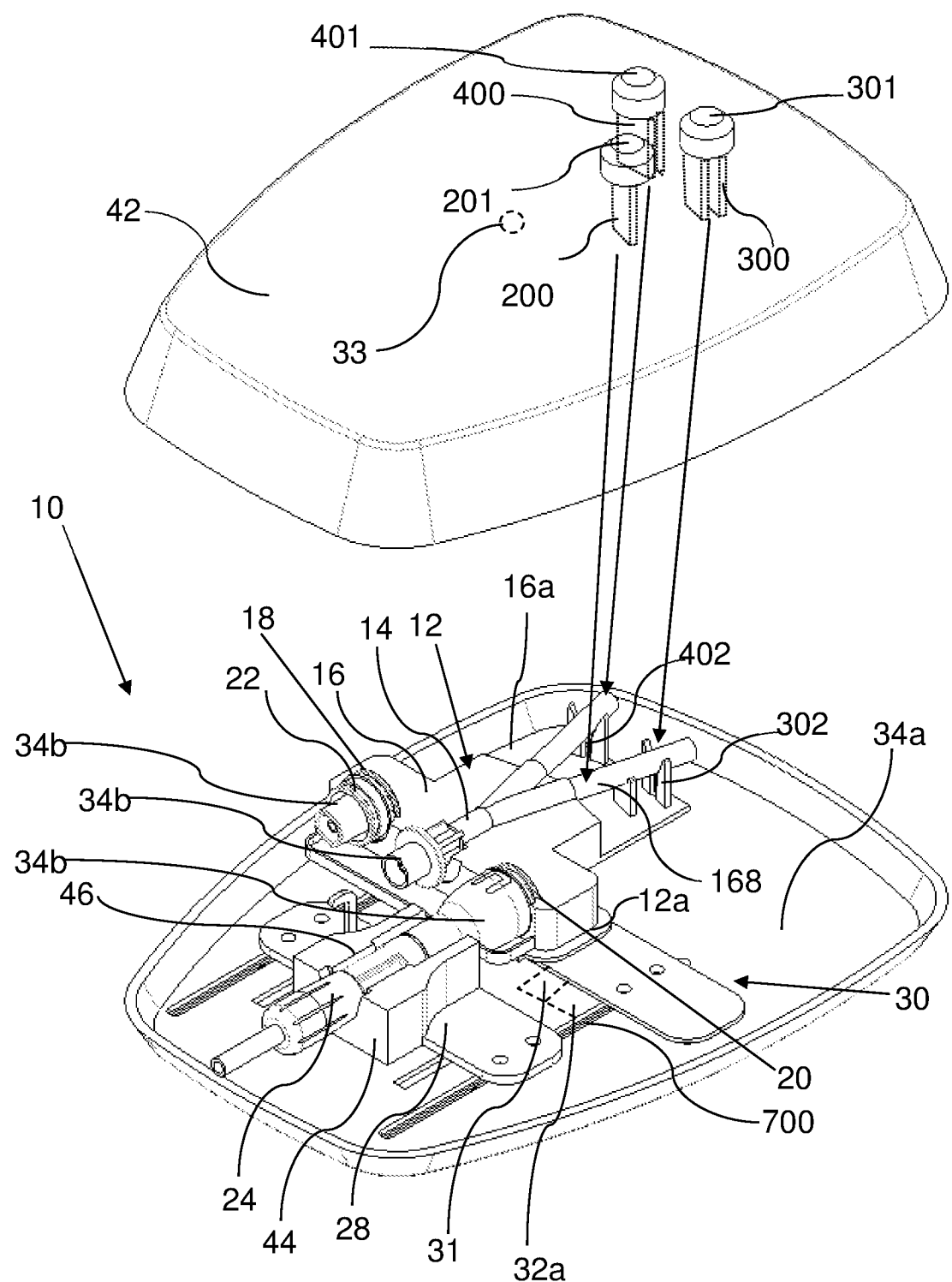
FIG. 21 is a perspective view of the apparatus of FIGS. 19 and 20 with elevated cover.

Further, also in the embodiment according to FIGS. 19 to 26 the apparatus 10 may comprise a radiation source 33 (e.g. an ultraviolet light source) for irradiating components of the apparatus 10 with radiation (e.g. ultraviolet light) having an antibacterial effect. For example such a radiation source 33 is indicated in FIGS. 19 and 21. Again, the apparatus 10 may comprise one or several reflective surfaces 34a being configured to reflect said radiation of source 33 as indicated e.g. in FIG. 19 or (as an addition or an alternative) in FIG. 21.

Figure 22:
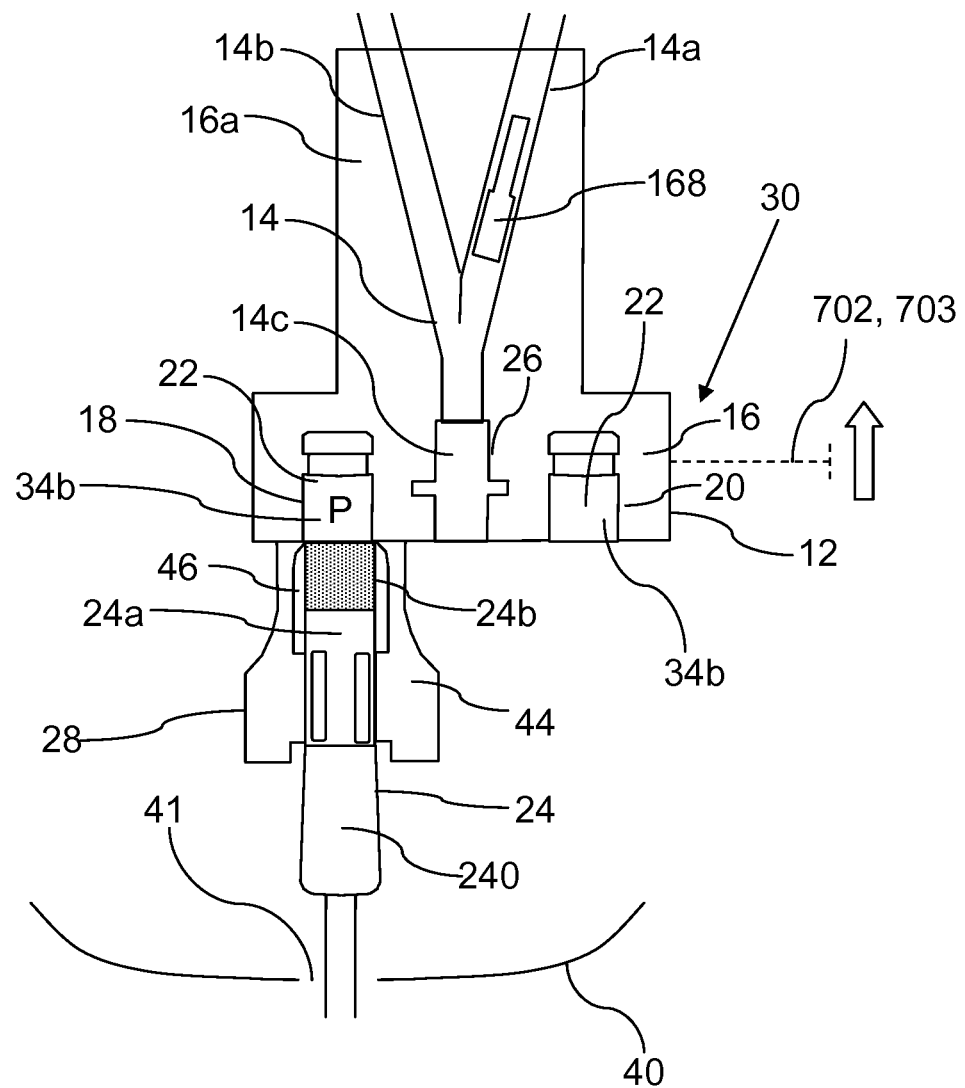

Further as indicated in FIGS. 21 and 22, the apparatus 10 may comprise a surface 34b comprising a disinfectant admixture, particularly comprised by a coating of said surface 34b or an additive to the (e.g. molding) material of the surface 34*b* in order to reduce contamination with germs. Particularly the surface 34*b* may be a surface 34*b* of said end caps 22 and/or of the tubular fitting 24, particularly of its first and/or second portion 24*a*, 24*b*, particularly of said adapter 24*b* (see below).

Further, preferably, the body 16 can be released from a carrier 12*a* of the cradle assembly 12, which carrier is movable in said Position P, P', P''. In this way, the body 16 can be formed as a consumable that can be easily removed from the housing 40 of the apparatus 10. For instance, carrier 12*a* or body 16 may be moveably supported on a guiding element that allows movement between the positions P, P' and P''', which guiding element may in turn be movably support on a further guiding means that allows movement of the carrier 12*a*/body 16 towards and away from the holder assembly 28. Holder assembly 28 may be movably supported on a separate or said further guiding means. Holder assembly 28 may be driven by the cradle assembly (e.g. by carrier 12*a* or body 16), but may also be independently driven.

Further, said holder assembly 28 includes a body 44 having an opening 46 for receiving the tubular fitting 24. The tubular fitting may comprise recesses for engaging with the body 44 in the region of said opening 46 of the body 44.

Furthermore, as indicated in FIGS. 22 to 26, the cradle assembly 12 is configured to be movable in each of said positions P, P', P''' towards and away from the holder assembly 28 by means of said means 30 (e.g. by using said actuating means 702 and particularly handle 703. Other ways of actuation are also conceivable. Particularly, in each of said positions, the cradle assembly is moveable towards and away from the holder assembly 28 in a direction perpendicular to said transverse direction. Particularly, for guiding said movement of the cradle assembly 12 and of the holder assembly 28, the apparatus 10 comprises a guiding means 700 as indicated in FIG. 21, for instance.

Figure 23:
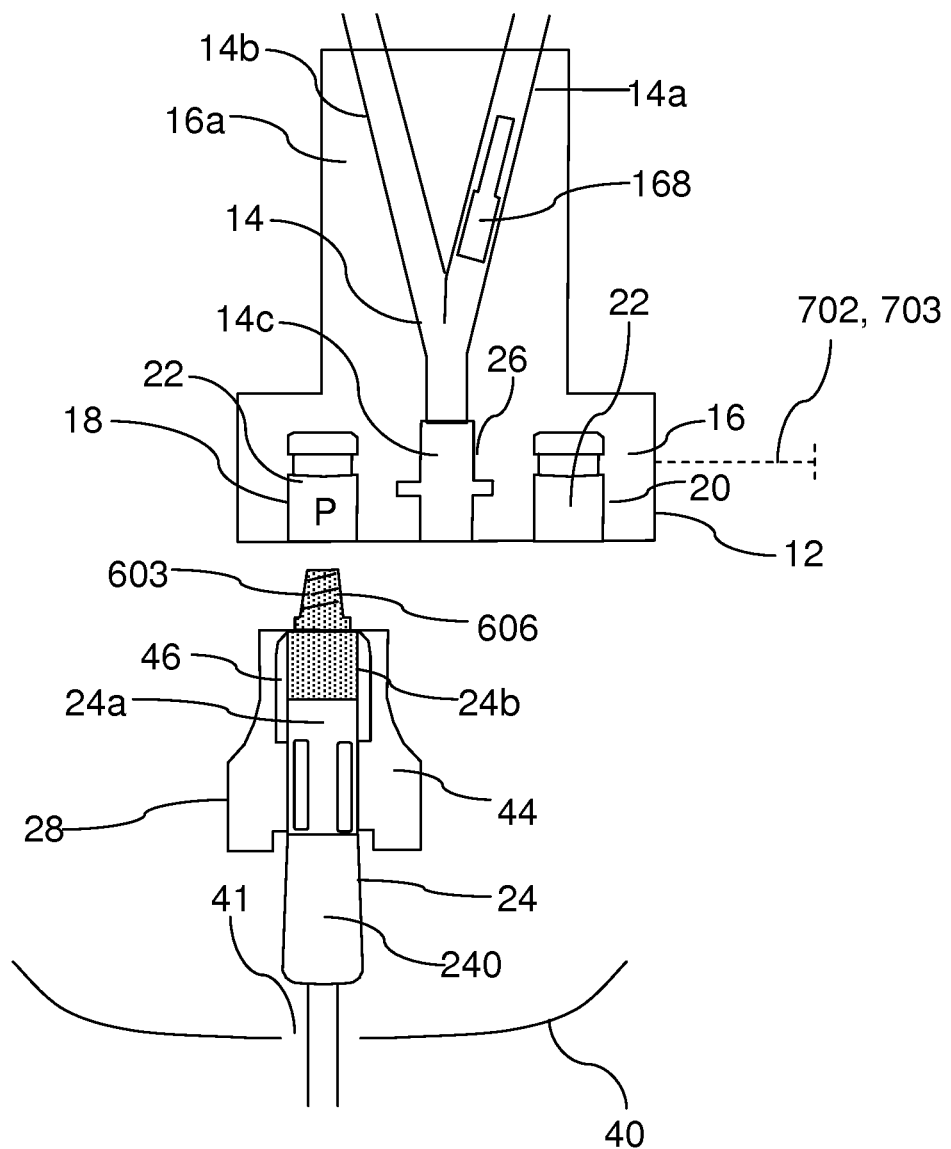

Particularly, when the cradle assembly 12 is in the first position P, as shown in FIG. 21, the cradle assembly 12 is movable away from the holder assembly 28, as indicated by the arrow, so as to unfasten an end cap 22 received in the first port 18 that is fastened to the tubular fitting 24 from said tubular fitting 24, which in turn is inserted into the holder assembly 28, namely in the corresponding opening 46 (cf. FIG. 23).

From there, the cradle assembly 12 is moveable into the second (transverse) position P' as well as towards the holder assembly 28 so as to connect a connector 14 inserted into the connector holder 26 to the tubular fitting 24 so that a flow connection is established between said connector 14 and the tubular fitting 24 so that a flow connection can be established between the tubular fitting 24 and the connector 14. When the fluid delivery procedure (which will be described below) is over, the cradle assembly 12 is moveable away from the holder assembly 28 as indicated by the arrow shown in FIG. 25, so as to disconnect the connector 14 from the tubular fitting 24.

As shown further shown in FIG. 21, the apparatus 10 comprises an openable or removable cover 42 of the housing 40. The cover 42 is preferably at least partially or completely transparent, particularly so as to be able to observe the fastening/unfastening of the end caps 22 and the connecting of the tubular fitting 24 to the connector 14 as well as the disconnecting of the tubular fitting 24 from the connector 14. Further, preferably, the holder assembly 28 and/or the cradle assembly 12 are removably mounted in the housing 40.

Figure 27:
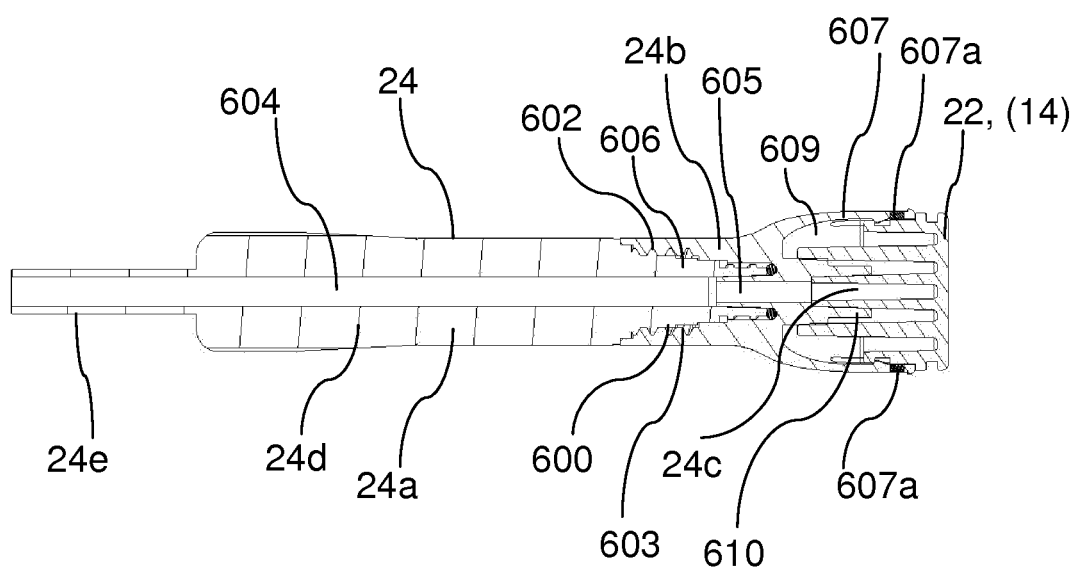
FIG. 27 shows a cross-sectional view of an adapter according to the invention.
Figure 28:
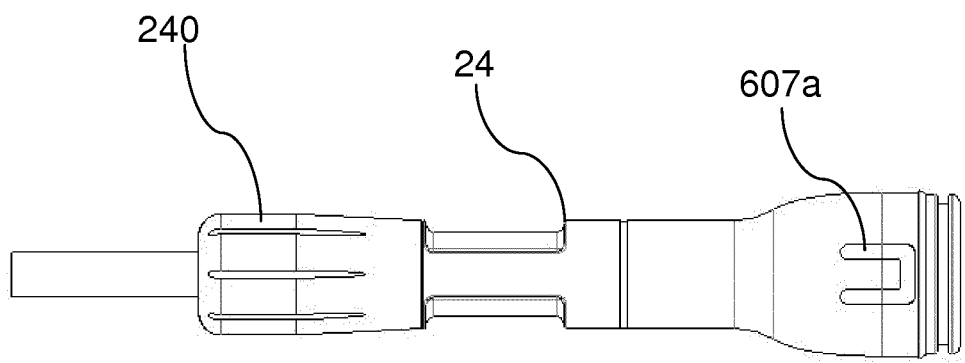
FIG. 28 shows a lateral view of the adapter of FIG. 27.

Now, as particularly shown in FIG. 24, the holder assembly 28 is configured to move together with the cradle assembly 12 when the cradle assembly 12 is in the second position (the holder assembly 28 may be taken along by the cradle assembly 12 upon movement of the cradle assembly 12 towards the holder assembly 28), such that a member 240 of the tubular fitting 24 protrudes at least partially out of the housing 40 (this member 240 is also shown in FIGS. 27 and 28), e.g. through a through hole 41 formed in the housing 40. Thus, the member 240 is accessible from outside the housing 40 when the tubular fitting 24 is connected to the connector 14 so that the tubular fitting can be opened (e.g. by rotating member 240) and fluid can pass the tubular fitting 24.

Further, as indicated in FIG. 25, when the cradle assembly 12 is in the second position P' and is moved away from the holder assembly 28, the holder assembly 28 moves with the cradle assembly 12 in the beginning so that said member 240 is again positioned inside a compartment defined by the housing 40 and cannot be rotated from outside the housing 40 to ensure that the tubular fitting 24 that has been closed by means of member 240 before disconnecting the tubular fitting 24 from the connector cannot be opened again so that fluid can be lost. Further, from the position shown in FIG. 25, the cradle assembly is movable into the third position and towards the holder assembly 28 as shown in FIG. 26 so that a new end cap 22 that is arranged in the second port 20 can be fastened to the tubular fitting 24. In this position, the member 240 protrudes again out of the housing 40 through opening 41.

Furthermore, for operating the connector 14, the apparatus 10 comprises a support 16*a* forming preferably a part of body 16 of the cradle assembly 12. Thus the support 16*a* may be integrally formed with the body 16 and can thus be a consumable, too The support 16*a* is configured to support a first conduit 14*a* of the connector 14, which first conduit 14*a* comprises a frangible inline seal 68 and may be connected to a fluid bag containing the fluid that is to be guided via the connector 14 and the tubular fitting 24 as well as a catheter 24*e* connected to the tubular fitting or comprising the latter towards a patient. The support 16*a* is further configured to support a second conduit 14*b* of the connector 14, wherein the two conduits 14*a*, 14*b* branch off from an end section 14*c* of the connector 14 (cf. e.g. FIGS. 22 to 26), via which end section 14*c* the connector 14 is configured to be connected to the tubular fitting 24.

When the tubular fitting 24 has been connected to the connector 14 as intended (which is shown in FIGS. 21 and 24), a first actuating member 200 is pressed via a button 201 so that said frangible inline seal 168 is broken. This allows flushing of the conduits 14*a*, 14*b* while the tubular member is still closed. Thus fluid (e.g. from a fluid bag) enters the first conduit 14*a*, is passed into the second conduit 14*b* and ends up e.g. in a fluid waste bag connected to the second conduit 14*b*.

When the conduits 14*a*, 14*b* have been flushed, a third actuating member 400 is pressed via a button 401 so as to interrupt the passage of fluid through the second conduit 14*b* being supported on said support 16*a*. To accomplish this, the third actuating member 400 is configured to press the second conduit 14*b* into an associated slot 402 of the support 16*a* so that the second conduit 14*b* is compressed and thereby sealed in the slot 402. Now, the member 240 is actuated and fluid passes from the first conduit 14*a* via the tubular fitting 24 to the catheter 24*e* of the patient.

Finally, to end fluid delivery, the member 240 is actuated to close the tubular fitting 24 and a second actuating member 300 (cf. FIGS. 21 and 24) is pressed via a button 301 so as to interrupt the passage of fluid through the first conduit 14*a* being supported on said support 16*a*. Again, to accomplish this, the second actuating member 300 is configured to press the first conduit 14*a* into an associated slot 401 of the support 16*a* so that the first conduit 14*a* is compressed and thereby sealed in the slot 401.

Now, as shown in FIGS. 25 and 26, the connecter 14 can be disconnected from the tubular fitting 24 and a new end cap 22 received in the second port 20 can be fastened to the tubular fitting 24.

It is to be noted, that the actuating members 200, 300, 400 are preferably mounted such to the housing 40 or with respect to the support 16 of the cradle assembly 12 that the support 16/cradle assembly 12 can move relative to the actuating members 200, 300, 400, but the latter are able to engage with the respective conduit 14*a*, 14*b* as described above, when the cradle assembly 12 resides in the second position P' and has been moved towards the holder assembly 28 so that the connector 14 is properly connected to the tubular fitting 24. This is shown in FIG. 21 by means of arrows indicating the respective points on the conduits 14*a*, 14*b* against which the respective actuating member 200, 300, 400 presses upon actuation.

Preferably, the buttons 201, 301, 401 are labeled by means of a pictogram, respectively, so as to describe their specific function to a user. This allows a description of the function of the buttons 201, 301, 401 that is independent of any language and universally understandable. Further, as shown particularly in FIGS. 27 and 28, the tubular fitting 24 may comprise an adapter 24*b* which forms itself an aspect of the present invention. Generally, the tubular fitting 24 comprises a first portion 24*a* that is configured to be connected to an end region 24*d* of a catheter 24*e* or is connected to a catheter 24*e* as well as a second portion 24*b* that is configured such that an end cap 22 or a connector 14 (not shown) can be fastened/connected to the second portion 24*b* by plugging the end cap 22 or connector 14 into an opening 24*c* of said second portion 24*b* (e.g. upon said movement of the cradle assembly 12 towards the holder assembly 28 when the cradle assembly 12 is in the corresponding position P, P"). Further, the second portion 24*b* is configured such that the end cap 22 or the connector 14 can be unfastened/disconnected from the second portion 24*b* by pulling the end cap 22/connector 14 out of said opening 24*c* (e.g. upon said movement of the cradle assembly 12 away from the holder assembly 28 when the cradle assembly 12 is in the respective position P', P").

The remarkably simple connection procedure is thus allowed due to the fact that the apparatus 10 according to FIGS. 21 to 28 uses a rotation-free plugging or pulling movement.

In order to use this kind of movement also with catheters 24*e* that comprise threads 603 and thus require rotation for making a connection to a connector 14, the second portion 24*b* may be formed as an adapter 24*b*.

This adapter 24*b* comprises according to FIGS. 27 and 28 a first recess 600 at a first end of the adapter 24*b*, which first recess 600 comprises an internal thread 602 configured to be rotationally fastened to said external thread 603 of the first portion 24*a* or—generally—to an end region 24*d* of a catheter 24*e* such that a lumen 604 surrounded by the first portion 24*a*/end region 24*d* is in flow communication with a lumen 605 surrounded by the adapter 24*b*. The first recess 600 may comprise a conical shape. Further, the external thread 603 may be formed on a correspondingly conical section 606 of the first portion 24*a*/end region 24*d*.

Preferably, the adapter 24*b* comprises a preferably bell-shaped shroud 607 at an opposite second end of the adapter 24*b*, which shroud 607 surrounds a second recess 609 of the adapter 24*b* into which second recess 609 a protrusion 610 of the adapter 24*b* protrudes, which protrusion 610 comprises an opening 24*c* of the adapter 24*b* for connecting to the connector 4 or end cap 22 as described herein.

Preferably, the shroud 607 surrounds said protrusion 610 and said opening 24*c* of the adapter 24*b* in order to provide an additional safety barrier against infections. In an embodiment of the present invention, the shroud may be omitted. Further, preferably, wherein the shroud 607 is coaxially arranged with respect to said protrusion 610. In order to securely fix the respective end cap 22 or connector 14 to the adapter 24*b* or tubular fitting 24, the end cap 22 and connector 14 are each configured to engage with a latching means 607*a* provided in the shroud 607 of the adapter 24*b* on opposite sides of the shroud (cf. FIGS. 27 and 28) upon plugging the end cap 22/connector 14 into the opening 24*c* of the adapter 24*b*/tubular fitting 24.

However, alternatively, the first portion 24*a* and the second portion 24*b* may also be integrally connected. Here, the catheter 24*e* may comprise a tubular fitting that requires no rotational fasting right from the start and an adapter is not necessary. In such an embodiment of the tubular fitting 24, the first portion 24*a* and the second portion 24*b* may form a continuous integral part having said opening 24*c* for making a connection to the end cap 22/connector 14 by means of the simple plugging movement described herein.

Also shown in FIG. 28 is said member 240 that is configured to be rotated so as to close or open the lumen 604 (see also above).

Figure 29:
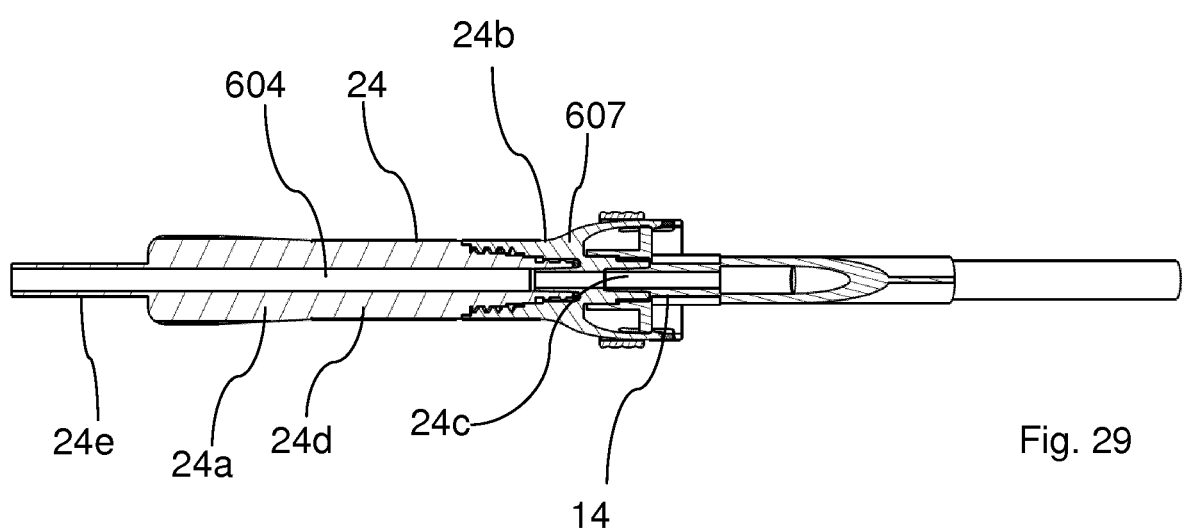
FIG. 29 shows a cross-sectional view of the adapter of FIG. 27 when the connector is plugged into the adapter.

Further, FIG. 29 shows the adapter/second portion 24*b* when a connector 14 is connected/plugged into the opening 24*c* of the adapter/second portion 24*b*.

Most preferably, in the framework of the present invention as described herein, the connecting and/or disconnecting of connector 14 and tubular fitting 24 (as well as recapping) is performed by one of: a patient using the apparatus at home (e.g. a home dialysis patient), by a caregiver using the apparatus at the patient's home or within a health care facility, or by a healthcare professional using the apparatus at the patient's home or in a health care facility.

The invention claimed is:

1. An apparatus for connecting and disconnecting a tubular fitting (24) to a connector (14), the apparatus (10) comprising:
   a cradle assembly (12) configured for accommodating the connector (14), the cradle assembly (12) including a body (16) having:
   a first port (18) and a second port (20), said first and second ports being disposed at opposite ends of said body (16), the first port (18) being configured for receiving an end cap (22) to unfasten the end cap (22) from the tubular fitting (24) and the second port (20) being configured to receive a further end cap (22) to fasten the further end cap (22) to the tubular fitting (24), and
   a connector holder (26) being disposed between said first and second ports (18, 20), and configured for accommodating insertion of the connector (14);
   a holder assembly (28) configured for accommodating insertion of the tubular fitting (24); and
   the cradle assembly (12) being configured to perform a non-rotational movement in a transverse direction relative to said holder assembly (28) between a first position (P), a second position (P'), and a third position (P"), wherein the apparatus (10) comprises a cover (42) for covering the cradle assembly, and wherein the apparatus (10) comprises a first actuating member (200) that is arranged on the cover and configured to break a frangible inline seal (168) of a first conduit (14a) of the connector (14) when the connector (14) is inserted into the connector holder (26).

2. The apparatus of claim 1, wherein said holder assembly (28) includes a body (44) having an opening (46) for receiving the tubular fitting (24).

3. The apparatus of claim 1, wherein the cradle assembly (12) is configured to be movable in each of said positions (P, P', P") towards and away from the holder assembly (28) in a direction perpendicular to said transverse direction.

4. The apparatus of claim 1, wherein, when the cradle assembly (12) is in the first position (P), the cradle assembly (12) is movable away from the holder assembly (28) so as to unfasten the end cap (22) that is fastened to the tubular fitting (24).

5. The apparatus of claim 1, wherein, when the cradle assembly (12) is in the second position (P'), the cradle assembly (12) is movable towards the holder assembly (28) so as to connect the connector (14) to the tubular fitting (24) or is moveable away from the holder assembly (28) so as to disconnect the connector (14) from the tubular fitting (24).

6. The apparatus of claim 1, wherein the apparatus (10) comprises a housing (40), wherein the body (16) is configured to be releasably fastened to a carrier (12a) of the cradle assembly (12), so that the body (16) can be removed from the carrier (12a) and/or said housing (40).

7. The apparatus of claim 6, wherein the holder assembly (28) is configured to move together with the cradle assembly (12) when the cradle assembly (12) is in the third position (P''') such that a member (240) of the tubular fitting (24) protrudes out of the housing (40) when the tubular fitting (28) is inserted into the holder assembly (28) and fastened to the end cap (22) that is received in the second port (20), so that said member (240) can be actuated from outside the housing (40) so as to close the tubular fitting (24) for preventing passage of fluid through the tubular fitting (24).

8. The apparatus of claim 1, wherein, when the cradle assembly (12) is in the third position (P'''), the cradle assembly (12) is movable towards the holder assembly (28) so as to fasten the end cap (22) received in the second port (20) to the tubular fitting (24).

9. The apparatus of claim 1, wherein the body (16) of the cradle assembly (12) comprises a support (16a) for supporting the first conduit (14a) of the connector (14), which first conduit (14a) comprises the frangible inline seal (168), and for supporting a second conduit (14b) of the connector (14), wherein the two conduits (14a, 14b) branch off from an end section (14c) of the connector (14), via which end section (14c) the connector (14) is configured to be connected to the tubular fitting (24).

10. The apparatus of claim 9, wherein the apparatus (10) comprises the first actuating member (200) that is configured to break said frangible inline seal (168) when the cradle assembly (12) is in the second position (P') and the connector (14) inserted into the connector holder (26) is connected to the tubular fitting (24) inserted into the holder assembly (28).

11. The apparatus of claim 9, wherein the apparatus (10) comprises a second actuating member (300) that is configured to interrupt passage of fluid through the first conduit (14a) of the connector (14) being supported on said support (16a) when the cradle assembly (12) is in the second position (P') and the connector (14) inserted into the connector holder (26) is connected to the tubular fitting (24) inserted into the holder assembly (28).

12. The apparatus of claim 9, wherein the apparatus (10) comprises a third actuating member (400) that is configured to interrupt passage of fluid through the second conduit (14b) of the connector (14) being supported on said support (16a) when the cradle assembly (12) is in the second position (P') and the connector (14) inserted into the connector holder (26) is connected to the tubular fitting (24) inserted into the holder assembly (28).

13. The apparatus of claim 1, wherein said apparatus (10) comprises the tubular fitting (24), two end caps (22), and the connector (14).

14. The apparatus of claim 13, wherein the tubular fitting (24) comprises a first portion (24a) and an adjacent second portion (24b) comprising an opening (24c).

15. The apparatus of claim 14, wherein the second portion (24b) is configured such that the end cap (22) received in the second port (20) can be fastened to the second portion (24b) by plugging the end cap (22) into said opening (24c) of said second portion (24b), and wherein the second portion (24b) is configured such that the end cap (22) received in the first port (18) can be unfastened from the second portion (24b) by pulling the end cap (22) out of said opening (24c).

16. The apparatus of claim 15, wherein said plugging and/or said pulling is irrotational.

17. The apparatus of claim 14, wherein the second portion (24b) is configured such that the connector (14) can be connected to the second portion (24b) by plugging the connector (14) into said opening (24c) of said second portion (24b), and wherein the second portion (24b) is configured such that the connector (14) can be disconnected from the second portion (24b) by pulling the connector (14) out of said opening (24c).

18. The apparatus of claim 14, wherein the second portion (24b) is formed as an adapter, which comprises a first recess (600) at a first end of the adapter (24b), which first recess (600) comprises an internal thread (602) configured to be rotationally fastened to an external thread (603) of the first portion (24a), and wherein the adapter (24b) comprises a shroud (607) at an opposite second end of the adapter (24b), which shroud (607) surrounds a second recess (609) of the adapter (24b) into which a protrusion (610) of the adapter (24b) protrudes, which protrusion (610) comprises said opening (24c) of the adapter (24b) such that the shroud (607) surrounds said protrusion (610) and said opening (24c) of the adapter (24b), wherein the shroud (607) is coaxially arranged with respect to said protrusion (610).

19. The apparatus of claim 14, wherein the second portion (24b) is integrally connected to the first portion (24a), wherein preferably the second portion (24b) comprises a shroud (607), which shroud (607) surrounds a recess (609) of the second portion (24b) into which a protrusion (610) of the second portion (24b) protrudes, which protrusion (610) comprises said opening (24c) of the second portion (24b) such that the shroud (607) surrounds said protrusion (610) and said opening (24c) of the second portion (24b), wherein the shroud (607) is coaxially arranged with respect to said protrusion (610).

20. The apparatus of claim 1 wherein said body (16) is an elongate body (16).

21. The apparatus of claim 1, wherein at least one of said first and second ports (18, 20) has an insertable sleeve (122, 124) configured for receiving the end cap (22) of the tubular fitting (24).

22. The apparatus of claim 21, wherein at least one of said first and second ports (18, 20) has a one-way directional mechanism (146) for selectively rotating said insertable sleeve (122, 124) in one direction while preventing motion in an opposite direction during operation.

23. The apparatus of claim 21, wherein at least one of said first and second ports (18, 20) has at least one one-directional tooth (148) on said at least one of said first and second ports (18, 20), and at least one complementary one-directional tooth (150) on said corresponding sleeve (122, 124).

24. The apparatus of claim 1, wherein said first port (18) has a first sleeve (122) being slidably insertable in said first port (18), and configured for receiving the end cap (22) of the tubular fitting (24) to rotationally unfasten the end cap (22) from the tubular fitting (24).

25. The apparatus of claim 1, wherein said second port (20) has a second sleeve (124) being slidably insertable in said second port (20), and configured for receiving a replacement cap (126) of the tubular fitting (24) to rotationally fasten the replacement cap (126) upon the tubular fitting (24).

26. The apparatus according to claim 1, wherein the apparatus (10) comprises a surface (34b) comprising a disinfectant admixture comprised by a coating of said surface (34b) or comprised by an additive to a molding material of said surface (34b) in order to reduce contamination with germs.

27. The apparatus of claim 1, further comprising an adapter (24b) for connecting an end region (24d) of a conduit (24e) comprising an external thread (603) to the connector (14) that is configured to be plugged into an opening (24c) of the adapter (24b), so that a flow communication is established between said conduit (24e) and the connector (14) via said adapter (24b), the adapter (24b) further comprising: a first recess (600) at a first end of the adapter (24b), which first recess (600) comprises an internal thread (602) configured to be rotationally fastened to said external thread (603) of said conduit (24e), and a shroud (607) at an opposite second end of the adapter (24b), which shroud (607) surrounds a second recess (609) of the adapter (24b) into which a protrusion (610) of the adapter (24b) protrudes, which protrusion (610) comprises said opening (24c) of the adapter (24c), such that the shroud (607) surrounds said protrusion (610) and said opening (24c) of the adapter (24b), wherein the shroud (607) is coaxially arranged with respect to said protrusion (610).

28. A method for connecting and disconnecting a tubular fitting (24) to a connector (14), wherein the connector (14) is connected to the tubular fitting (24) and/or disconnected from the tubular fitting (24) using the apparatus (10) according to claim 1.

29. The method of claim 28, wherein the connecting and/or disconnecting is performed by one of: a patient at home, a caregiver at the patient's home or within a health care facility, by a healthcare professional at the patient's home or in the health care facility.

30. The method of claim 28, wherein the connector (14) comprises the first conduit (14a), which first conduit (14a) comprises the frangible inline seal (168), and a second conduit (14b), wherein the two conduits (14a, 14b) branch off from an end section (14c) of the connector (14), which end section (14c) is configured to be connected to the tubular fitting (24) or disconnected from the tubular fitting (24), and wherein the tubular fitting (24) comprises a member (240) which is configured to be actuated so as to open or close the tubular fitting (24) for allowing or preventing passage of fluid through the tubular fitting (24), the method comprising the further steps of:

providing the tubular fitting (24) with the end cap (22) fastened to the tubular fitting (24), wherein the end cap (22) is received in the first port (18) of the body (16) of the cradle assembly (12) residing in the first position (P), and wherein the tubular fitting (24) is inserted into the holder assembly (28), moving the cradle assembly (12) away from the holder assembly (28) so as to unfasten the end cap (22) from the tubular fitting (24), moving the cradle assembly (12) into the second position (P') and then towards the holder assembly (28) so as to connect the connector (14) inserted into the connector holder (26) to the tubular fitting (24), breaking the frangible inline seal (168) using the first actuating member (200), flushing both conduits (14a, 14b) by letting fluid flow through the first and the second conduit (14a, 14b) while the tubular fitting (24) is closed for preventing the passage of fluid through the tubular fitting (24), interrupting the second conduit (14b) by actuating a third actuating member (400) and opening the tubular fitting (24) by actuating said member (240) of the tubular fitting (24), letting fluid pass through the first conduit (14a), the end section (14c), and the tubular fitting (24) towards a target, closing the tubular fitting (24) by actuating said member (240) of the tubular fitting (24), interrupting the first conduit (14a) for preventing the passage of fluid through the first conduit (14a) by actuating a second actuating member (300), closing the tubular fitting (24) for preventing passage of fluid through the tubular fitting (24), moving the cradle member (12) away from the holder assembly (28) so as to disconnect the connector (14) from the tubular fitting (24), moving the cradle assembly (12) into the third position (P''') and towards the holder assembly (28) to as to fasten the end cap (22) received in the second port (20) to the tubular fitting (24).

* * * * *